United States Patent
Yadav et al.

(10) Patent No.: US 11,622,981 B2
(45) Date of Patent: Apr. 11, 2023

(54) BACTERIAL STRAIN USEFUL FOR TREATMENT OF AGE-RELATED CONDITIONS

(71) Applicant: Wake Forest University Health Sciences, Winston-Salem, NC (US)

(72) Inventors: Hariom Yadav, Winston-Salem, NC (US); Shaohua Wang, Winston-Salem, NC (US); Ravinder Nagpal, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 16/947,866

(22) Filed: Aug. 21, 2020

(65) Prior Publication Data
US 2021/0052677 A1 Feb. 25, 2021

Related U.S. Application Data

(60) Provisional application No. 62/890,984, filed on Aug. 23, 2019.

(51) Int. Cl.
| | | |
|---|---|---|
| *A61K 35/747* | (2015.01) | |
| *A61K 9/00* | (2006.01) | |
| *A61K 9/19* | (2006.01) | |
| *A61P 1/00* | (2006.01) | |
| *A61P 29/00* | (2006.01) | |
| *A23L 33/135* | (2016.01) | |
| *A23L 33/00* | (2016.01) | |
| *A61K 31/7032* | (2006.01) | |
| *A61K 35/00* | (2006.01) | |

(52) U.S. Cl.
CPC .......... *A61K 35/747* (2013.01); *A23L 33/135* (2016.08); *A23L 33/40* (2016.08); *A61K 9/0056* (2013.01); *A61K 9/19* (2013.01); *A61K 31/7032* (2013.01); *A61P 1/00* (2018.01); *A61P 29/00* (2018.01); *A23V 2002/00* (2013.01); *A23Y 2220/63* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 9,937,211 B2 | 4/2018 | Kelly et al. | |
| 2013/0202571 A1* | 8/2013 | Bhunia | A61K 35/747 424/93.45 |

FOREIGN PATENT DOCUMENTS

| | | |
|---|---|---|
| KR | 1020110113026 A | 10/2011 |
| WO | 2018161077 A1 | 9/2018 |

OTHER PUBLICATIONS

Azad et al. "Probiotic Species in the Modulation of Gut Microbiota: An Overview", Biomed Res Int, 2018:9478630 (2018).
Bahitham et al. "Liver-specific expression of carboxylesterase 1g/esterase-x reduces hepatic steatosis, counteracts dyslipidemia and improves insulin signaling", Biochim Biophys Acta, 1861(5): 482-490 (2016).
Borta et al. "Inhibitory avoidance, pain reactivity, and plus-maze behavior in Wistar rats with high versus low rearing activity", Physiology & Behavior, 84(3): 387-396 (2005).
Buford, Thomas W. "(Dis)Trust your gut: the gut microbiome in age-related inflammation, health, and disease", Microbiome, 5:80 (2017) (11 pages).
Cani et al. "Changes in Gut Microbiota Control Metabolic Endotoxemia-Induced Inflammation in High-Fat Diet-Induced Obesity and Diabetes in Mice", Diabetes, 57(6): 1470-1481 (2008).
Caporaso et al. "QIIME allows analysis of high-throughput community sequencing data", Nat Methods, 7(5): 335-336 (2010).
Crowther et al. "Fluorometric assay of O-linked glycoproteins by reaction with 2-cyanoacetamide" Anal Biochem, 163(1): 170-174 (1987).
Dahl et al. "Body mass index across midlife and cognitive change in late life" International Journal of Obesity, 37(2): 296-302 (2012).
Dao et al. "Akkermansia muciniphila and improved metabolic health during a dietary intervention in obesity: relationship with gut microbiome richness and ecology" Gut, 65: 426-436 (2016).
Dejesus et al. "Associations between anxiety disorder diagnoses and body mass index differ by age, sex and race: a population based study" Clin Pract Epidemiol Ment Health, 12: 67-74 (2016).
Dominguez et al. "The biology of the metabolic syndrome and aging" Curr Opin Clin Nutr Metab Care, 19(1): 5-11 (2016).
Everard et al. "Cross-talk between Akkermansia muciniphila and intestinal epithelium controls diet-induced obesity" Proc Natl Acad Sci USA, 110(22): 9066-9071 (2013).
Gaffney, Christopher J., et al., "Methods to assess subcellular compartments of muscle in C. elegans", J Vis Exp, 93: e52043 (2014) (11 pages).
Hanzelmann et al. "Toll-like receptor 2 activation depends on lipopeptide shedding by bacterial surfactants" Nat Commun, 7: 12304 (2016) (11 pages).
Hess et al. "Lipoteichoic acid deficiency permits normal growth but impairs virulence of *Streptococcus pneumoniae*" Nat Commun, 8: 2093 (2017) (13 pages).
Hong et al. "Lipoteichoic acid of *Streptococcus mutans* interacts with Toll-like receptor 2 through the lipid moiety for induction of inflammatory mediators in murine macrophages" Mol Immunol, 57(2) :284-291 (2014).
Kawai et al. "The role of pattern-recognition receptors in innate immunity: update on Toll-like receptors" Nat Immunol, 11(5): 373-384 (2010).

(Continued)

*Primary Examiner* — Oluwatosin A Ogunbiyi
(74) *Attorney, Agent, or Firm* — Myers Bigel, P.A.

(57) ABSTRACT

Provided is a composition comprising an isolated *Lactobacillus paracasei* D3.5 strain or cellular components thereof. In some embodiments, the composition is provided in a pharmaceutically acceptable carrier, which may be a food product, tablet or capsule suitable for enteral administration, etc. Also provided is a composition comprising lipoteichoic acid isolated from *Lactobacillus paracasei* D3.5 strain, which may be provided in a pharmaceutically acceptable carrier.

18 Claims, 16 Drawing Sheets

(56) References Cited

OTHER PUBLICATIONS

Kelly et al. "Breaking down the barriers: the gut microbiome, intestinal permeability and stress-related psychiatric disorders" Front Cell Neurosci, 9: 392 (2015) (20 pages).
Kim et al. "Antitumor activity of Lactobacillus plantarum cytoplasm on teratocarcinoma-bearing mice" J. Microbiol. Biotechnol., 12(6): 998-1001 (2002).
Kim et al. "Lipoteichoic acid from Lactobacillus plantarum inhibits the expression of platelet-activating factor receptor induced by Staphylococcus aureus lipoteichoic acid or Escherichia coli lipopolysaccharide in human monocyte-like cells" J Microbiol Biotechnol, 24(8): 1051-1058 (2014).
Landete et al. "Probiotic Bacteria for Healthier Aging: Immunomodulation and Metabolism of Phytoestrogens" Biomed Res Int, 2017: 5939818 (2017).
Mu et al. "Leaky Gut As a Danger Signal for Autoimmune Diseases" Front Immunol, 8:598 (2017) (10 pages).
Nagpal et al. "Gut microbiome and aging: Physiological and mechanistic insights" Nutr Healthy Aging, 4(4): 267-285 (2018a).
Nagpal et al. "Human-origin probiotic cocktail increases short-chain fatty acid production via modulation of mice and human gut microbiome" Sci Rep, 8: 12649 (2018b) (15 pages).
Naito et al. "A next-generation beneficial microbe: Akkermansia muciniphila" J Clin Biochem Nutr, 63(1): 33-35 (2018).
Nell et al. "Bacterial products increase expression of the human cathelicidin hCAP-18/LL-37 in cultured human sinus epithelial cells" FEMS Immunol Med Microbiol, 42(2): 225-231 (2004).
Ninkovic et al. "Differential effects of gram-positive and gram-negative bacterial products on morphine induced inhibition of phagocytosis" Sci Rep 6: 21094 (2016).
Nunes-Souza et al. "Aging Increases Susceptibility to High Fat Diet-Induced Metabolic Syndrome in C57BL/6 Mice: Improvement in Glycemic and Lipid Profile after Antioxidant Therapy" Oxid Med Cell Longev, 2016: 1987960 (2016) (18 pages).
Nunez, J., "Morris Water Maze Experiment" J Vis Exp, 19: e897 (2008).
Ottman et al. "Pili-like proteins of Akkermansia muciniphila modulate host immune responses and gut barrier function" PLoS One 12(3): e0173004 (2017) (18 pages).
Pelaseyed et al. "The mucus and mucins of the goblet cells and enterocytes provide the first defense line of the gastrointestinal tract and interact with the immune system" Immunol Rev, 260(1): 8-20 (2014).
Ribeiro et al. "Evolution of recognition of ligands from Gram-positive bacteria: similarities and differences in the TLR2-mediated response between mammalian vertebrates and teleost fish" J Immunol, 184(5): 2355-2368 (2010).
Schiffrin et al. "The inflammatory status of the elderly: the intestinal contribution" Mutat Res, 690(1-2): 50-56 (2010).
Schroeder et al. "Bifidobacteria or Fiber Protects against Diet-Induced Microbiota-Mediated Colonic Mucus Deterioration" Cell Host Microbe, 23(1): 27-40 e27 (2018).
Schwandner et al. "Peptidoglycan- and lipoteichoic acid-induced cell activation is mediated by toll-like receptor 2" J Biol Chem, 274(25): 17406-17409 (1999).
Sedor et al. "Reflotron cholesterol measurement evaluated as a screening technique" Clin Chem, 34(12): 2542-2545 (1988). Abstract.
Shimizu, Y. "Gut microbiota in common elderly diseases affecting activities of daily living" World J Gastroenterol 24 (42): 4750-4758 (2018).
Solis et al. "Measuring Caenorhabditis elegans life span in 96 well microtiter plates" J Vis Exp, 49: e2496 (2011) (6 pages).
Stehle, Jr. et al. "Lipopolysaccharide-binding protein, a surrogate marker of microbial translocation, is associated with physical function in healthy older adults" Journals of Gerontology Series A: Biomedical Sciences and Medical Sciences, 67(11): 1212-1218 (2012).
Tak et al. "NF-kappaB: a key role in inflammatory diseases" J Clin Invest, 107(1): 7-11 (2001).
Travassos et al. "Toll-like receptor 2-dependent bacterial sensing does not occur via peptidoglycan recognition" EMBO Rep, 5(10): 1000-1006 (2004).
Virta et al. "Midlife cardiovascular risk factors and late cognitive impairment" European Journal of Epidemiology, 28: 405-416 (2013).
Wang et al. "Lactobacillus rhamnosus GG supernatant upregulates serotonin transporter expression in intestinal epithelial cells and mice intestinal tissues" Neurogastroenterol Motil, 27(9): 1239-1248 (2015).
Wrzosek et al. "Transplantation of human microbiota into conventional mice durably reshapes the gut microbiota" Scientific Reports, 8: 6854 (2018) (9 pages).
Yadav et al. "Beneficial metabolic effects of a probiotic via butyrate-induced GLP-1 hormone secretion" J Biol Chem, 288(35): 25088-25097 (2013).
Yadav et al. "Protection from obesity and diabetes by blockade of TGF-beta/Smad3 signaling" Cell Metab, 14(1): 67-79 (2011).
Yemitan et al. "Neurosedative and muscle relaxant activities of aqueous extract of Bryophyllum pinnatum" Fitoterapia, 76(2): 187-193 (2005).
Zhou, K. "Strategies to promote abundance of Akkermansia muciniphila, an emerging probiotics in the gut, evidence from dietary intervention studies" J Funct Foods, 33: 194-201 (2017).
International Search Report and Written Opinion corresponding to PCT/US2020/47304; dated Jan. 19, 2021 (8 pages).

\* cited by examiner

A.

B.

C.

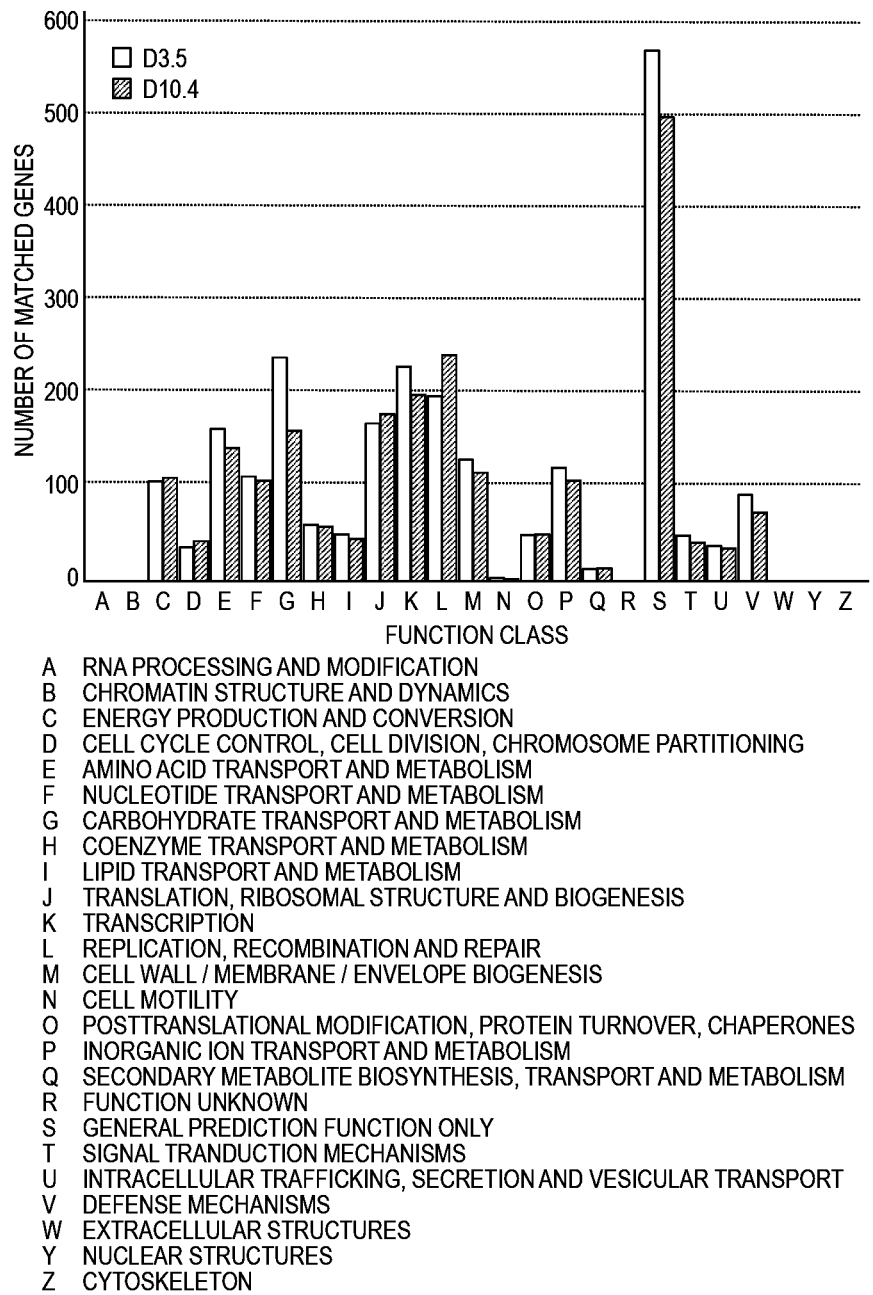

A RNA PROCESSING AND MODIFICATION
B CHROMATIN STRUCTURE AND DYNAMICS
C ENERGY PRODUCTION AND CONVERSION
D CELL CYCLE CONTROL, CELL DIVISION, CHROMOSOME PARTITIONING
E AMINO ACID TRANSPORT AND METABOLISM
F NUCLEOTIDE TRANSPORT AND METABOLISM
G CARBOHYDRATE TRANSPORT AND METABOLISM
H COENZYME TRANSPORT AND METABOLISM
I LIPID TRANSPORT AND METABOLISM
J TRANSLATION, RIBOSOMAL STRUCTURE AND BIOGENESIS
K TRANSCRIPTION
L REPLICATION, RECOMBINATION AND REPAIR
M CELL WALL / MEMBRANE / ENVELOPE BIOGENESIS
N CELL MOTILITY
O POSTTRANSLATIONAL MODIFICATION, PROTEIN TURNOVER, CHAPERONES
P INORGANIC ION TRANSPORT AND METABOLISM
Q SECONDARY METABOLITE BIOSYNTHESIS, TRANSPORT AND METABOLISM
R FUNCTION UNKNOWN
S GENERAL PREDICTION FUNCTION ONLY
T SIGNAL TRANDUCTION MECHANISMS
U INTRACELLULAR TRAFFICKING, SECRETION AND VESICULAR TRANSPORT
V DEFENSE MECHANISMS
W EXTRACELLULAR STRUCTURES
Y NUCLEAR STRUCTURES
Z CYTOSKELETON

FIG. 8

BACTERIAL STRAIN USEFUL FOR TREATMENT OF AGE-RELATED CONDITIONS

CROSS-REFERENCE TO RELATED APPLICATIONS

This application claims the benefit of U.S. Provisional Patent Application No. 62/890,984, filed Aug. 23, 2019, the disclosure of which is incorporated by reference herein in its entirety.

STATEMENT OF GOVERNMENT FUNDING

This invention was made with government support under grant R01DK081842 awarded by the National Institutes of Health, the Department of Defense funding W81XWH-18-1-0118, W81XWH-19-1-0236, R01AG018915, and Wake Forest Clinical and Translational Science Institute (WF CTSI) funded through NIH Grant Award Number UL1TR001420. The United States government has certain rights in the invention.

BACKGROUND

The numbers of older people (>65 years) are increasing around the world, and aging-related comorbidities such as obesity, diabetes, cardiovascular diseases, cancer, infections and cognitive decline are increasing in older adults. Common determinants and precise mechanism(s) of how aging contributes in these health ailments are not known, but low-grade inflammation is often higher in older adults and is a major risk factor for increasing mortality and morbidity in this age group.

Although the precise mechanisms that may trigger low-grade inflammation are still under study, increased gut permeability ("leaky gut") can allow non-selective diffusion of dietary and microbial antigens from the gut lumen, which may promote inflammatory response in the local (gut mucosa) and systemic immune systems. Emerging evidence suggests that detrimental perturbations in gut microbiome (dysbiosis) are associated with leaky gut, inflammation and poor health outcomes in older adults, indicating that gut therapies targeted to modulate the microbiome may ameliorate aging-related leaky gut and inflammation.

Gut permeability is normally tightly-controlled with intestinal barriers like tight junction proteins and a mucus layer. The mucus layer functions as a physical barrier to separate gut microbes and host cells, and protects from leaking and invading pathogens and antigens. The intestinal mucus layer covers the epithelial cells by making a viscoelastic gel layer, which is synthesized by goblet cells. Intestinal goblet cells are interspersed between epithelial cells on the villi of intestinal lumen and constantly secrete mucins to form the mucus layer. Mucin 2 (Muc2) is the major mucin secreted from intestinal goblet cells that forms major part of mucus layer in the gut, and it is known to protect leaky gut and invasion of microbes. Muc2 knockout (KO) mice develop colitis with a dramatic inflammatory gut mucosa that is linked to significant decreased thickness of mucus layer. The resulting thin mucus layer allows microbes of the gut to invade intestinal epithelial cells, activating an inflammatory response in immune cells. Similarly, the mucus layer thickness is dramatically reduced in the gut of older adults, and this is linked with increased leaky gut and inflammation. This evidences that the mucus layer plays an important role in regulating aging-related leaky gut and inflammation, and developing gut microbiota modulators that can promote mucin production can be beneficial to ameliorate aging-related leaky gut and inflammation.

Despite the growing acceptance of the importance of the gut barrier in diseases, knowledge of the underlying mechanism(s) that reinforce the barrier when faced with stressors is incomplete, and viable and practical strategies for pharmacologic modulation of the gut barrier remain unrealized. See WO 2018/161077 to Ghosh et al.

Probiotics are (generally live) bacteria that may exhibit health benefits to the host/consumers upon administering in sufficient amounts. Most commonly-used probiotics are strains that belong to the lactic acid bacteria category like lactobacilli and bifidobacteria, which have been reported to have beneficial effects in several human diseases, including aging-associated comorbidities. For example, Chen et al demonstrated that the *Lactobacillus* (L.) *paracasei* strain PS23 prevents aging-related muscle loss and mitochondrial dysfunction. Furthermore, LGG and *L. plantarum* inhibit the adherence of enteropathogenic *Escherichia* (E.) *coli* to the intestinal epithelial cells through induction of Muc2 and Muc3 mucin production.

Although the beneficial effects of probiotics may act in part by beneficially modulating the gut microbiota, the precise mechanisms of action remain largely unknown. Further, though probiotics are generally used as live cells, there is limited evidence suggesting that some specific strains of bacteria may also exhibit beneficial effects in dead form. Since commonly-used probiotics like lactobacilli and bifidobacteria are Gram positive, it has also been hypothesized that their bacterial cell ingredients like cell wall (peptidoglycan (PG), lipoteichoic acid (LTA) and proteins), cytoplasmic molecules and DNA may have biological activities.

SUMMARY

Herein we have demonstrated that a human-origin *L. paracasei* strain D3.5 (also called D3.5 hereafter), as well as the LTA from the cell wall of this strain, exhibit potent activity to stimulate mucin production and reduce aging-related leaky gut and inflammation.

Accordingly, provided herein according to some embodiments is a composition comprising an isolated *Lactobacillus paracasei* D3.5 strain or cellular components thereof. In some embodiments, the composition is provided in a pharmaceutically acceptable carrier.

In some embodiments, the carrier comprises a food product. In some embodiments, the strain is provided in a form suitable for enteral (e.g., oral) administration.

In some embodiments, the strain is lyophilized or freeze-dried. In some embodiments, the strain is non-viable (e.g., heat killed).

In some embodiments, the strain is present in the composition in a pharmaceutically effective amount (e.g., an amount effective to increase gut mucin production and/or to treat leaky gut and/or inflammation). In some embodiments, the strain is present in the composition in an amount of from 1 million to 10 trillion.

In some embodiments, the composition comprises cell wall components purified from the isolated *Lactobacillus paracasei* D3.5 strain.

Also provided is a composition comprising lipoteichoic acid isolated from a *Lactobacillus paracasei* D3.5 strain. In some embodiments, the composition is provided in a pharmaceutically acceptable carrier.

In some embodiments, the carrier comprises a food product. In some embodiments, the lipoteichoic acid is provided in a tablet or capsule suitable for enteral (e.g., oral) administration.

In some embodiments, the lipoteichoic acid is lyophilized or freeze-dried.

In some embodiments, the lipoteichoic acid is present in the composition in a pharmaceutically effective amount (e.g., an amount effective to increase gut mucin production and/or to treat age-relate leaky gut).

Further provided is a method of increasing gut mucin production in a mammalian subject in need thereof, comprising administering to the subject a therapeutically effective amount of the composition as taught herein, wherein said administering is by enteral administration. In some embodiments, the administering is by oral administration.

Also provided is a method of treating a gastrointestinal condition or inflammation in a mammalian subject in need thereof, comprising administering to the subject a therapeutically effective amount of the composition as taught herein, wherein said administering is by enteral administration. In some embodiments, the administering is by oral administration. In some embodiments, the treatment is for an age-related gastrointestinal condition such as leaky gut, metabolic dysfunction and/or inflammation.

BRIEF DESCRIPTION OF THE DRAWINGS

FIG. 8. The whole genome of L. paracasei D3.5 and L. paracasei D10.4 were sequenced in GENEWIZ, assembled and annotated with two separate pipeline one is a combination of CD-HIT, Augustus, and NRdatabase program while the second is PATRIC program. The sequences genome information is submitted to GenBank database with accession number L. paracasei D3.5: JAACXY000000000.1 and L. paracasei D10.4: JAAFGQY00000000. Both the genomes were classified in 26 COG functional class in the identified orthogonal sequences with the respective match of genes. The whole genome of L. paracasei D3.5 contains the extra genes contributing to the functional class of E, G, K and S corresponding to Amino acid transport and metabolism, carbohydrate transport and metabolism, coenzyme transport and metabolism and other prediction functions, respectively. Notably, all the reported extra COGs in the strain D3.5 contains the metabolism of specific genes. In the other strain of D10.4, three class of C, D, and L to functional class of energy production and conversion, cell cycle control, cell division, chromosome partitioning and replication, recombination and repair. These results indicate the contribution of more genes of the cell division cycle in strain D10.4 in comparison to strain D3.5.

DETAILED DESCRIPTION

Figure 1:
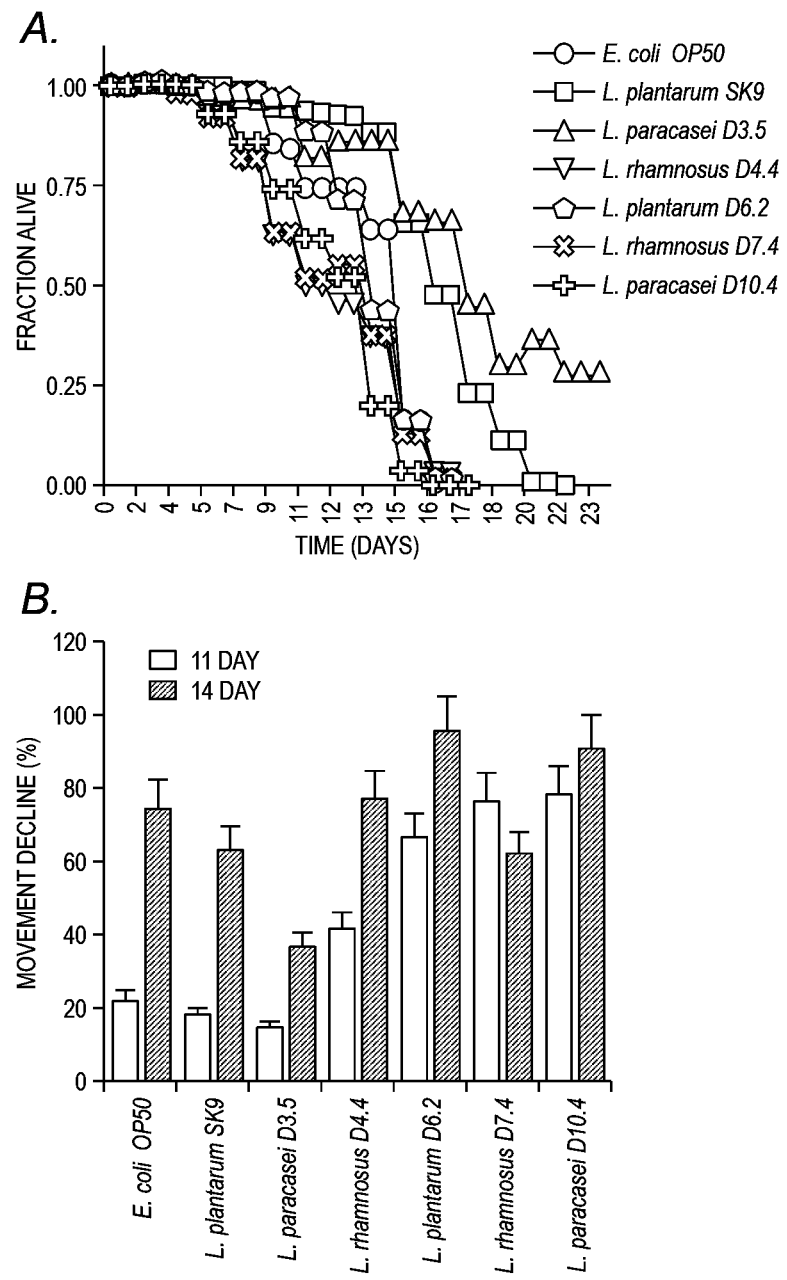
FIG. 1. Effects on aging in C. elegans and older mice. (A) Lifespan determination of C. elegans worms treated with different Lactobacillus strains and the E. coli control strain. (B) Movement decline of C. elegans fed with different strains on the 11th and 14th day. (C, D) Fasting blood glucose (columns) and glucose changes during the OGTT and ITT test. (E, F) Crown like structures (CLS) in the mice from D3.5 group are obvious less than that from the control group in liver and white adipocyte tissue histology by heatoxyline and eosin (H&E) staining. (G) Frequency distribution of adipocyte size. (H) Average cell size of adipocyte in the control and D3.5 group. Data are presented as mean±SD. *P<0.05, **P<0.001, ns, P>0.05.
Figure 1:
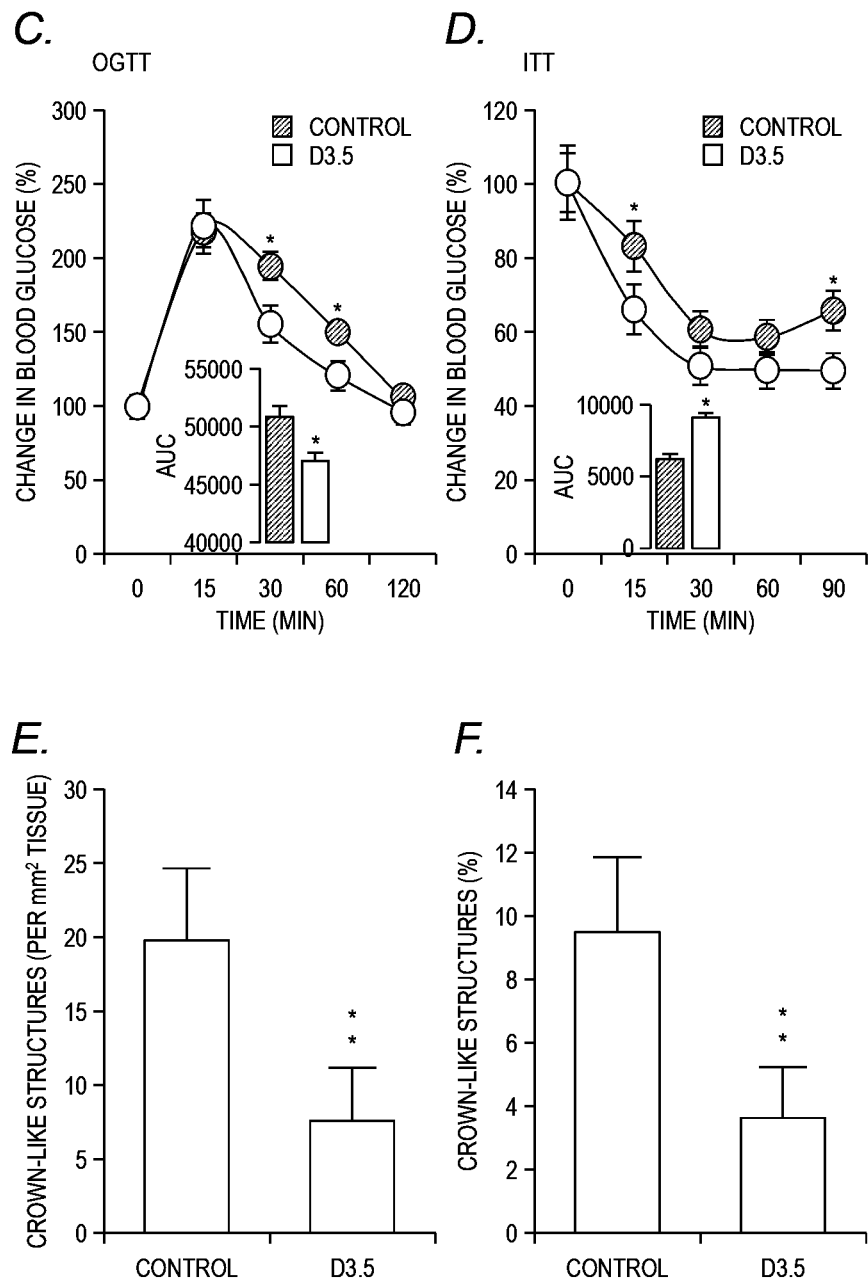
Figure 1:
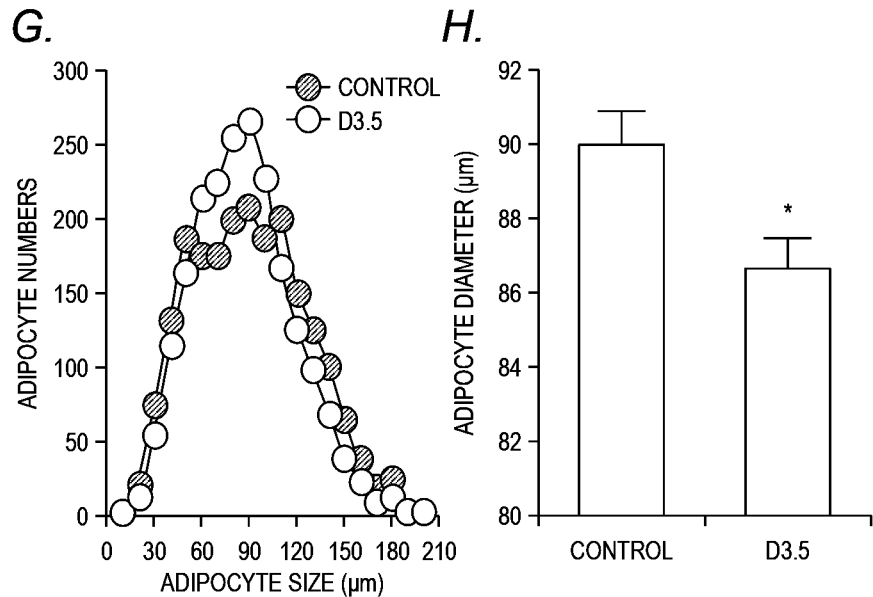

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise.

"Subject" or "patient" as used herein are generally mammalian or other animal subjects, including both human subjects and non-human mammalian subjects (e.g., dog, cat, horse, goat, sheep, camel, lamas, pig, etc.), avian subjects, aquatic subjects such as fish, etc., for research and/or veterinary purposes. Subjects may be male or female and may be of any suitable age, including neonate, infant, juvenile, adolescent, adult, and geriatric subjects; however in some embodiments the subject is an adult or geriatric subject. In some embodiments, the subject is a human subject that is 65 years of age or older. In some embodiments, the subject may have one or more comorbidities such as diabetes, obesity, physical disability, etc.

"Treat" as used herein refers to any type of treatment that imparts a benefit to a subject, particularly for alleviating gastrointestinal conditions such as leaky gut. For example, the treatment may increase intestinal mucin production and/or reduce aging-related leaky gut and inflammation, etc. Treatment also includes prophylactic treatment of a subject deemed to be at risk of developing an age-related gastrointestinal condition such as leaky gut and/or inflammation.

"Leaky gut" as used herein refers to a condition in which the gut barrier is impaired by loosening of epithelial cell-cell junctions and/or thinning of the layer of mucin that covers the epithelium of the intestinal tract. An impaired gut barrier (i.e., leaky gut) may be a major contributor to the initiation and/or progression of various chronic diseases, which may also be associated with aging, including, but not limited to, metabolic endotoxemia, type II diabetes, fatty liver disease, obesity, atherosclerosis, inflammatory bowel diseases, Alzheimer's disease, Parkinson's disease, cardiovascular diseases, certain cancers, and other inflammatory diseases.

Provided herein is an isolated human-origin *Lactobacillus paracasei* D3.5 strain useful for treating gastrointestinal conditions such as age-related leaky gut. The strain is deposited in the American Type Culture Collection (ATCC), 10801 University Blvd., Manassas, Va., 20110-2209, on Jun. 8, 2022, as Accession No. PTA-127306. Complete genomic sequence information for the human-origin *Lactobacillus paracasei* D3.5 strain has been deposited and is accessible at NCBI at GenBank assembly accession: GCA_009996805.1, and methods of isolation are described in Nagpal et al., Scientific Reports (2018) 8:12649.

The strain may be provided live or dead, as it has been found in the data presented herein that the strain in dead form provides alleviation of age-related leaky gut and inflammation. Thus, the strain may be in the form of a live bacterial population, a non-viable (i.e., dead) bacterial preparation, or some or all of the cellular components thereof (e.g., cell wall components, which have been separated from cytoplasm components in dead bacterial cells). In some embodiments, the population, preparation or components are provided in lyophilized or freeze-dried form, or supplemented in food products like yogurt, cheese, fermented milk, ice-cream, chocolates and other food/beverage forms. Where the strain is in the form of a non-viable bacterial preparation, it may be heat-killed bacteria, irradiated bacteria and/or lysed bacteria, and can be used to supplement in drinks/beverages, baked foods, dietary and herbal supplements, bakery products and any type of food ingredients.

Also provided herein according to some embodiments is isolated lipoteichoic acid (LTA) from the human-origin *Lactobacillus paracasei* D3.5 strain useful for treating gastrointestinal conditions such as leaky gut and/or inflammation.

Another aspect of the invention relates to a composition comprising the strain, components thereof or LTA therefrom and a pharmaceutically or nutritionally acceptable carrier. Suitable carriers may include, but are not limited to, excipients and diluents. Examples of suitable carriers include lactose, starch, glucose, methyl cellulose, magnesium stearate, mannitol, sorbitol and the like. Examples of suitable diluents include ethanol, glycerol and water (e.g., sterile or purified water).

The compositions may also comprise suitable binder(s), lubricant(s), suspending agent(s), coating agent(s), solubilizing agent(s), etc. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like.

Preservatives, stabilizers, dyes and/or flavoring agents may be provided in the composition, if desired. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption and that are used as standard in the food industry. Typical nutritionally acceptable carriers, diluents and excipients will be familiar to the skilled person in the art.

In some embodiments the composition is suitable to be administered orally (e.g. tablet, capsule, powder, food product), enterally (e.g. with a feeding tube) or rectally (e.g. enema). For example, the composition may be an edible composition in that it is suitable for human or animal consumption.

Another aspect of the invention relates to a probiotic composition comprising the human-origin *Lactobacillus paracasei* D3.5 strain. As used herein, the term "probiotic"

means microbial cell preparations or components of microbial cells with a beneficial effect on the health or well-being of the host. See U.S. Pat. No. 9,937,211. The probiotic composition may be an orally administrable composition of metabolically active, i.e., live and/or or lyophilized, or non-viable (i.e., dead) bacteria. The probiotic composition may contain other ingredients, and may be provided in a suitable oral dosage form, e.g., in the form of a tablet, capsule, sachet, food product or powder (e.g. in a salt shaker).

Suitable dosages of the strain or components thereof may include $10^6$ (one million), $10^7$, $10^8$ or $10^9$ to $10^{11}$, $10^{12}$, or $10^{13}$ (ten trillion) bacterial counts or their equivalent cellular components such as LTA.

A further aspect of the invention relates to food products, dietary supplements, nutraceuticals, nutritional formulae, drinks and medicaments comprising the human-origin *Lactobacillus paracasei* D3.5 strain, components thereof or LTA therefrom, and use thereof. Examples of specific food products that are applicable to the present invention include milk-based products, ready-to-eat desserts and/or baked products, powders for re-constitution with, e.g., beverages such as milk or water, chocolate milk drinks, malt drinks, ready-to-eat dishes, instant dishes or drinks for humans or food compositions representing a complete or a partial diet intended for pets or livestock. This includes food products that may not be suitable for inclusion of live probiotics, as it has be found that the strain taught herein is beneficial even in its non-viable form.

The present invention is explained in greater detail in the following non-limiting examples.

EXAMPLES

Example 1: Human-Origin *Lactobacillus paracasei* D3.5 Ameliorates Aging-Related Leaky Gut Via Enhancing Mucin Production Leaky gut and increased inflammation are major risk factors for morbidity and mortality in older adults. In this study, we demonstrated that a human-origin *Lactobacillus paracasei* D3.5 strain (called D3.5 hereinafter) in dead form extended the life span of *C. elegans* and prevented decline in physical function and muscle mass. In addition, feeding of D3.5 to older mice (>79 weeks) prevented high fat diet (HFD)-induced metabolic dysfunctions and improved physical and cognitive functions that were associated with decreased leaky gut and inflammation. Mucin degrading bacteria *Akkermansia muciniphila* abundance was significantly increased upon D3.5 feeding that was associated with increased mucin production. Mechanistically, Lipoteichoic acid (LTA), a cell wall component of D3.5 cells, enhances mucin (Muc2) expression via activating TLR-2/P38-MAPK pathway, which, in turn, reduces leaky gut and inflammation.

Our results demonstrate that D3.5 is beneficial for ameliorating aging-related leaky gut and inflammation.

Methods

*C. elegans* culture and longevity assay. The life span screening procedure was carried out in liquid medium in 96-well plates according to an established protocol described in detail by Solis on JoVe (Sedor et al. 1988). In summary, 10-17 age-synchronized animals (L1 larva) were cultured in S-complete media containing Ampicillin, Carbenicillin and Amphotericin B in wells of 96-well plates. Wells were supplemented with different feeding bacteria including *E. coli* OP50 as a control and 6 mentioned isolated lactobacilli strains ($0.3 \times 10^8$ cfu/mL). To prevent self-fertilization, fluorodeoxyuridine (FUDR) was added 36 h after seeding (100 ug/mL final). The number of live worms was counted daily on the basis of body movement using a microscope and the fraction of animals alive was scored as a function of time. *C. elegans* strains used in this study were N2 and MAH19, which has GFP fusion proteins localized to muscle (purchased from CGC). Body length of the treated worms during life span was measured through analyzing pictures using ImageJ software. Movement was measured as described by Gaffney et al. (PMID: 25489753). The number of strokes of at least 12 treated worms in each treatment group were counted in 1 min. One leftward and one rightward bend was considered as one stroke. For pumping rate, the number of pharyngeal contractions of 12 randomly selected nematodes was counted under the microscope for 1 min.

Preparation of dead probiotic strain. The probiotic strain *Lactobacillus paracasei* D3.5 was prepared as described before (Nagpal et al. 2018b). After being cultivated in MRS at 37° C. for 6-8 h, cells were collected through centrifugation, washed twice with PBS (0.1 M, pH 7.4) and resuspended in 1/10 volume of PBS with 20% glycerol. Then, the suspension was treated under 70° C. for two hours. The cultures before and after heat treatment were serial diluted, spread onto MRS agar and cultivated for 12-24 h to get the cell concentration and detect the inactivation of heat treatment, respectively.

Cell wall, cytoplasm, peptidoglycan and lipoteichoic acid preparation. Cell wall and cytoplasm were prepared as described by Kim et al. (J. Microbiol. Biotechnol. 12(6), 998-1001, 2002) with modifications. *L. paracasei* D3.5 was cultivated in MRS at 37° C. to the logarithmic phase, then was harvested by centrifugation (2,000 g, 10 min). The pellets were resuspended in citrate buffer (50 min, pH 4.7) to 50 mg/ml (wet weight), followed by being disrupted four times with high pressure homogenizer (EmulsiFlex®-C3, AVESTIN, Inc., Canada). Cell debris were removed by centrifugation, and the supernatant was centrifuged again at 70,000 g for 30 min using an ultracentrifuge. The resulting supernatant was designated as the cytoplastic fraction, while the pellet was the crude cell wall sample. Peptidoglycan-wall teichoic acid (PGN-WTA) was extracted with SDS according to the protocol developed by Heß et al. (2017). After removing the cell debris as described above, SDS was added to the supernatant at a final concentration of 4%. Then, the solutions were incubated at 100° C. for 30 min, followed by being stirred overnight at room temperature. Through centrifugation (30,000 g, 15 min), pellets were washed four times with citrate buffer, and five times with ethanol. The crude PGN-WTA powder was obtained through lyophilization.

Lipoteichoic acid (LTA) fraction was extracted according to description elsewhere (Heft et al. 2017). *L. paracasei* D3.5 culture was disrupted as described above, the solutions were then stirred with an equal volume of butanol at room temperature for 30 min. Phase was separated through centrifugation at 21,000 g for 15 min. Then the aqueous phase containing LTA was collected and dialyzed (3.5 kDa cutoff membrane) against water which was changed every 24 h. After 5 days of dialysis, LTA solution was lyophilized to get the crude LTA powder.

Mice experiment. Aged (78-week-old) male C57BL/6J mice were purchased from Jackson Laboratory (Bar Harbor, Me., USA) and were maintained under a reverse light-dark cycle. Two groups were set up according to their body weight. Mice feeding with high-fat diet (60 kcal % fat) were started at the age of 80 weeks. Meanwhile, the dead probiotic strains (heat-treated *L. paracasei* D3.5) was given to the D3.5 group through water feeding (final concentration equal to $10^9$ cfu/ml before heat treatment), while equal amount of 20% glycerol was given as the control group named as CTL. The special water was changed daily during the whole period (16 weeks). Body weight and food intake were determined weekly in the first 8 weeks before starting other tests to avoid being disturbed. Water intake was determined daily and special water was changed. GTT, ITT, behavior test, gut permeability assays were carried out starting from the 9th week. Thereafter, tissues and macrophages were collected at week 16.

For fecal microbiome transplant, microbiome from control (CCTL) and D3.5 treated group (CD3.5) were prepared from 500 mg of fecal samples with 5 ml of reduced PBS (phosphate buffer supplemented with 0.1% Resazurin (w/v) and 0.05% L-cysteine-HCl) under anaerobic condition. Fecal microbiome transplant was carried out as described by Wrzosek et al. (2018a). Special water including antibiotics (Ampicillin, 1 g/l; Metronidazole, 1 g/l; Neomycin, 1 g/l and Vancomycin 0.5 g/l) as well as Sweetener (3 g/l) were used to feed C57BL/6 mice (6-8 week) for 4 days to remove the native microbiome, followed by bowel cleaning with PEG on the 5th day. After PEG treatment, fresh prepared CCTL and CD3.5 were transplanted through oral gavage (200 μl/mouse) for four continuous days. Tissues were collected after one week from the first dose of transplant. To explore the pathway through which the probiotic strain works, C57BL/6 and TLR2 KO mice (6-8 week) were separated into three groups according to body weight. For each group, water (control), dead *L. paracasei* D3.5 ($10^{11}$ cfu/ml before heat treatment) and LTA (6 mg/ml), were fed respectively based on the body weight (4 ml/kg) through oral gavage every day for 5 days. On the 5th day, fecal samples and intestine were collected for further analysis. All the animal experiments and procedures were approved by the IACUC of Wake Forest ARP.

Glucose and insulin tolerance tests. Insulin and glucose tolerance test (ITT and GTT) were carried out after 8 weeks treatment (Bahitham et al. 2016). Mice were fasted for 4-6 hours (ITT) and 10-12 h (GTT) before receiving oral gavage of glucose (2 g/kg body weight) and injection with Insulin (1 U/kg body weight), respectively. Tail blood was collected before and at 15, 30, 60 and 120 min after administration and glucose concentration was determined with a Truetrack® glucose meter (Nipro Diagnostics, Fort Lauderdale, Fla.).

Behavior studies. Open field test was performed in a quiet and dimly room. Mice were placed individually into the center of a white cylindrical tank (30 cm height×50 cm diameter). The tank was cleaned with 70% ethanol before the next test. Each experiment was monitored using camera for 5 min. ToxTrac (Rodriguez et al., Methods Ecol. Evol. 9:460-464, 2018) was used to track mice and analyze behavior parameters such as average speed, total distance travelled, percentage distance in the center and percentage time in the center, etc. Spatial memory and learning ability was tested through Morris water maze experiment according to the method described by Joseph Nunez (Nunez 2008). Tests were carried out in a white cylindrical tank (30 cm height×50 cm diameter) filled with tap water (25° C.) about 1 inch below the rescue platform. During the pre-training, each mouse was trained three times in different directions. The water maze testing was performed at the same time next day with the same condition. Mice undergo 12 trails from four different directions. Time used for each of them reach the platform in 30 s were recorded.

Inclined screen test. This test was performed according to Randall et al. with minor modification. Groups of mice (n=8) were left on a glass plane, inclined at 30° and the time taken for each mouse to slide off the screen was recorded 30 min after treatment with this test was carried out 30 min after treatment with BPE (50, 100, 200 mg/kg), diazepam (1 mg/kg, i.m.) or saline (Yemitan and Salandeen 2005).

Gut permeability assay. Intestinal permeability was performed with FITC-dextran (3-5 kDa; Sigma-Aldrich FD4) as described (Cani et al. 2008). Mice were fasted for 4-6 h, and were then given oral gavage with FITC-dextran (1 g/kg body weight). Blood was collected from the tip of tail vain after 4 h, followed by being centrifuged at 5,000 rpm for 10 min. The plasma was diluted properly with Fetal Bovine Serum (FBS), and the fluorescence intensity was determined with a fluorescence spectrophotometer (excitation, 485 nm; emission, 520 nm). Standard curve for calculating FITC-dextran concentrations were prepared through serial dilution of FITC-dextran in FBS.

Gut microbiome analyses. Gut microbiome was analyzed as described before (Scientific reports, Nagpal et al. 2018b). Genomic DNA were extracted from around 100 mg of mice feces using the Qiagen DNA Stool Mini Kit (Qiagen, CA, USA) according to the manufacturer's instructions. Primers 515 F (barcoded) and 806 R were used to amplify the V4 region of bacterial 16S rDNA (Caporaso et al. 2010). After being purified and quantified with AMPure® magnetic purification beads (Agencourt) and Qubit-3 fluorimeter (InVitrogen), respectively, Equal amounts (8 pM) of the amplicons were applied for sequencing on an Illumina MiSeq sequencer (using Miseq reagent kit v3). The sequences were de-multiplexed, quality filtered, clustered, and analyzed with the Quantitative Insights into Microbial Ecology (QIIME, version 1.9.1) software.

Fecal mucin assay. Fecal mucin concentration was determined using a fluorometric assay kit (Fecal Mucin Assay kit; Cosmo Bio co. LTD) that discriminates O-linked glycoproteins (mucins) from N-linked glycoproteins was used to quantify mucin within the feces (Crowther and Wetmore 1987).

SCFA measurements. To determine the influence of the dead probiotic strain on the organic acids/SCFAs production, fecal samples were collected weekly during the first 8 weeks. As described before (Scientific Reports, Nagpal et al. 2018b), 50 mg feces were grounded with a pellet pestle motor, followed by being resuspended in 1 mL PBS buffer (0.1 M, pH 7.4). After 4 h dissolution with 1 min vortex every 20 min, samples were centrifuged (12, 000 g, 10 min) and passed through the 0.45 μm membrane filter. Cell-free samples were used for determining the concentrations of SCFA (acetate, propionate and butyrate) as well as lactate using a high-performance liquid chromatography (Waters-2695 Alliance HPLC system, Waters Corporation, Milford, Mass., USA) with DAD detector at 210 nm, equipped with a Aminex HPX-87H column (Bio-Rad Laboratories, Hercules, Calif.). Sample (10 μL) was injected each time and $H_2SO_4$ (0.005 N) was used to elute the column with a flow rate of 0.6 mL/min at 35° C.

Cell culture and treatment. The mouse rectal cancer cell line CMT-93, was obtained from the American Type Culture Collection (Rockville, Md., USA). CMT-93 was grown in Dulbecco's modified Eagle's medium (DMEM, Sigma-Aldrich) supplemented with 10% heat-inactivated fecal calf serum (Invitrogen) and 1% penicillin-streptomycin (100×, Sigma-Aldrich) in 5% $CO_2$ at 37° C. After growing in 12-well plate (for RNA extraction) and 6-well plate (for protein extraction) for 24 h, cells were treated with 1% (v/v)

of cell wall, cytoplasm, PGN-WTA or LTA. Cell wall, PGN-WTA and LTA were resuspended in the original volume like cytoplasm to make the constitute ratio of different parts close to the natural composition in the strain. Cells were collected after 14 h treatment, RNA and proteins were prepared for real time PCR and western blotting, respectively. To explore the role of TLR2 pathway, TLR2 inhibitor (CU CPT22, 8 µM) was also added to inhibit the pathway during LTA treatment. Meanwhile, mucin proteins expressed by cells with the same treatments were also detected with the Periodic Acid-Schiff (PAS) Kit (Sigma). Briefly, cells were fixed with 10% buffered formalin phosphate for 1 h, stained with periodic acid stain for 5 min, stained with Schiff's reagent for 15 min, and washed three times with distilled water between each staining step. Images were taken under AmScope microscope at 4× magnification.

Real-time PCR. Total RNA was extracted from cells or tissues using RNeasy kit (Qiagen Inc., USA), and reverse transcription was performed with high-capacity cDNA reverse transcription kit (Applied Biosystems). The generated cDNA template, and primers for Muc 2, IL-6, IL-1β and TNFα were used in the real-time PCR according to the manuscript introduction (TaqMan Gene Expression Assays). 18S rRNA was used as an internal control. Relative gene expression was calculated using ΔΔCT procedure and presented as relative fold change.

Western blots. Protein extraction was performed with homogenization lysis buffer as described before (Yadav et al. 2013; Yadav et al. 2011). For protein extraction from cells, the harvested cells were resuspended in homogenization lysis buffer, followed by sonication treatment. Supernatant after centrifugation was used for western blot analysis. Expression of Mucin 2 (MUC 2) was analyzed by western blot with antibody from Sigma. In order to compare the expression difference of proteins in TLR2 pathway, phospho-p38 MAPK, p38-MAPK, phospho-SAPK/JNK, SAPK/JNK as well as NF-kB p65 were also analyzed with western blot using the corresponding antibodies purchased from Cell Signaling (Danvers, Mass.). Meanwhile, Tubulin was selected as the control protein. Band intensities were determined using ImageJ software and presented as fold change.

Histological analyses. For histological investigations, livers, white adipose tissue and intestinal tissues from mice were collected, washed with PBS and 10% formalin, followed by being fixed overnight in 10% formalin and embedded in paraffin blocks. Sections cut at 0.5 µm thickness were stained with Hematoxylin and eosin (H&E). Images were taken under AmScope microscope on 10× or 20× magnification using 9MP digital camera. Adipocyte sizes and distribution were determined as adipocyte diameter of 480 random adipocytes from each mouse with ImageJ software. Crown-like structures (CLS), indicative of inflammatory macrophages surrounding dead adipocytes, were identified based on aggregates of nucleated cells surrounding individual adipocytes. Crown-like structure density was obtained by counting the total number in each section compared with the total number of adipocytes.

To compare the goblet cell number, sections cut from Ileum were stained with Alcian Blue/PAS according to the technical Memo from newcomer Supply (Newcomer Supply, Middleton, Wis.). Images were taken on 10× magnification, and goblet cells (blue dots under the pink background) were counted by a blind person.

Whole genome sequencing and proteomics analysis. To compare the difference between L. paracasei D3.5 and L. paracasei D10.4 and explore the potential probiotic mechanism, genomic DNA from the two strains were extracted with QIAamp® DNA Mini Kit. Then DNA samples were sent to GeneWiz, Inc (South Plainfield, N.J., USA) for library preparation and next-generation sequencing. Sequences were assembled, annotated and analyzed with PATRIC online software (patricbrc.org). Protein expression differentia was analyzed using Uniprot (uniprot.org).

Results

1. Dead L. paracasei D3.5 feeding extends lifespan in Caenorhabditis (C.) elegans. C. elegans is a widely-used animal model in several anti-aging screening studies. Therefore, we screened our selected six best probiotic Lactobacillus strains (L. plantarum SK9, L. plantarum D6-2, L. paracasei D3.5, L. paracasei D10.4, L. rhamnosus D4-4, and L. rhamnosus D7-4) isolated from infant gut (Nagpal et al., Scientific Reports 8:12649, 2018) using wild-type C. elegans N2 (Solis and Petrascheck 2011. To control the wide differences of bacterial genera and species, in this screening, we included two strains from same genera and species, but different strains.

Interestingly, the only two strains of dead probiotics like L. paracasei D3.5 and L. plantarum SK9 feeding extended lifespan of wild type C. elegans N2, in which D3.5 exhibited highest effects (FIG. 1, panel A), while other strains either from same genera and species and/or distinct, show no significant changes on the lifespan of C. elegans compared to control bacteria (E. coli OP50 strain) fed C. elegans. These results indicate that (i) certain dead probiotics are beneficial to the aging; and (ii) these beneficial effects are very strain-specific not all probiotics from same genus and species exhibit beneficial effects against aging.

To determine the differences between two strains of L. paracasei (D3.5 and D10.4), we performed whole genome sequencing (WGS) and whole cell unbiased proteomics. Interestingly, we found 8.2% unique genes in D3.5 versus D10.4 while comparing WGS data. Similarly, D3.5 and D10.4 also showed 18.3% unique, 16.2% downregulated and 14.3% upregulated proteins in proteomics analyses. These differences may be an indicator of the reason in the differences of biological activities of two very similar genera and species of probiotics.

2. D3.5 feeding prevents HFD-induced metabolic dysfunctions in older mice. Based on the compelling beneficial effects of D3.5 feeding on the lifespan extension of C. elegans, we investigated its effects in older mice that were fed with HFD. Interestingly, 10 weeks of D3.5 feeding prevented development of glucose intolerance (measured by glucose tolerance test [GTT]) and insulin resistance (assayed by insulin tolerance test [ITT]) in HFD-fed older mice (FIG. 1, panels C and D). Body weight, food intake and energy expenditure were not significantly changed after D3.5 treatment compared to control older mice (data not shown), suggesting that D3.5 feeding improved glucose homeostasis and insulin sensitivity independent of changes in adiposity, food intake and energy expenditure. Further, feeding of D3.5 significantly reduced hepatic steatosis indicated by fat accumulation in the liver, with decreased crown like structures (indicator of inflammation) in the white adipose tissue (WAT) (FIG. 1, panels E and F). WAT adipocyte size was also significantly reduced in D3.5 fed older mice compared to controls (FIG. 1, panels G and H). Overall, these results demonstrate that the D3.5 feeding prevented HFD-induced glucose intolerance, insulin resistance, hepatic steatosis, and inflammation in WAT with small adipocytes, indicating that D3.5 feeding ameliorate detrimental metabolic effects in older mice.

Figure 2:
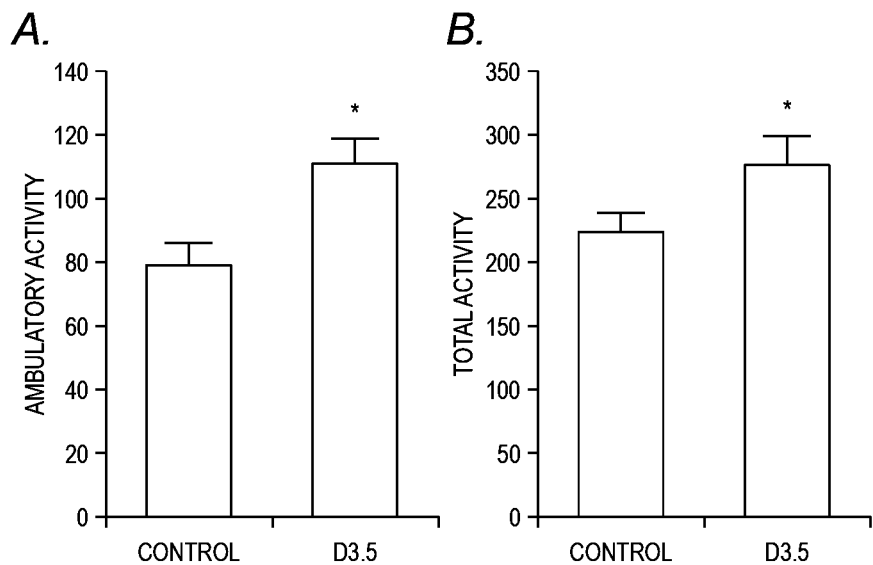
FIG. 2. Effects of D3.5 on behavior, gut permeability and expression of immune factors in the older mice. Ambulatory activity (A) and total activity (B) were increased in the D3.5 treated group (n=6). (C) Mice from the D3.5 group (n=6) showed more robust performance than mice from the control group in the inclined screen (4 limb hang). (D) Less rearing times were observed in the D3.5 group indicating the anxiety reduction effects of dead L. paracasei D3.5. (E) Data analysis from open field test with ToxTrac with percentage of time in the center. (F) Memory improvement analysis based on learning ability through Morris water maze. (G) Gut permeability in the D3.5 is relieved with 50% lower concentration of FITC leaked to blood. (H) Immune factors IL-6 and (I) IL-1β were reduced significantly in the colon of D3.5 treated group. Data are presented as mean±SD. *P<0.05, **P<0.001.
Figure 2:
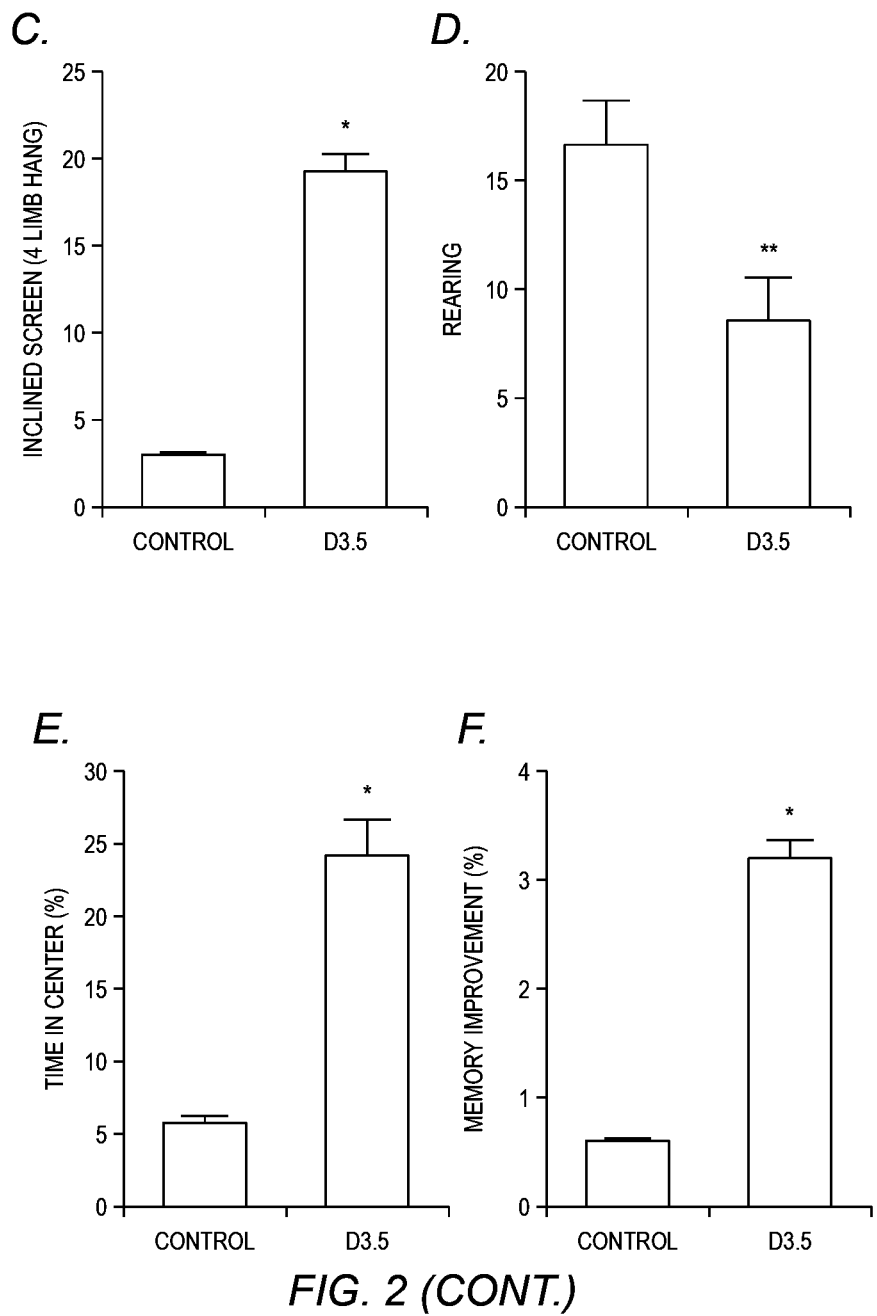
Figure 2:
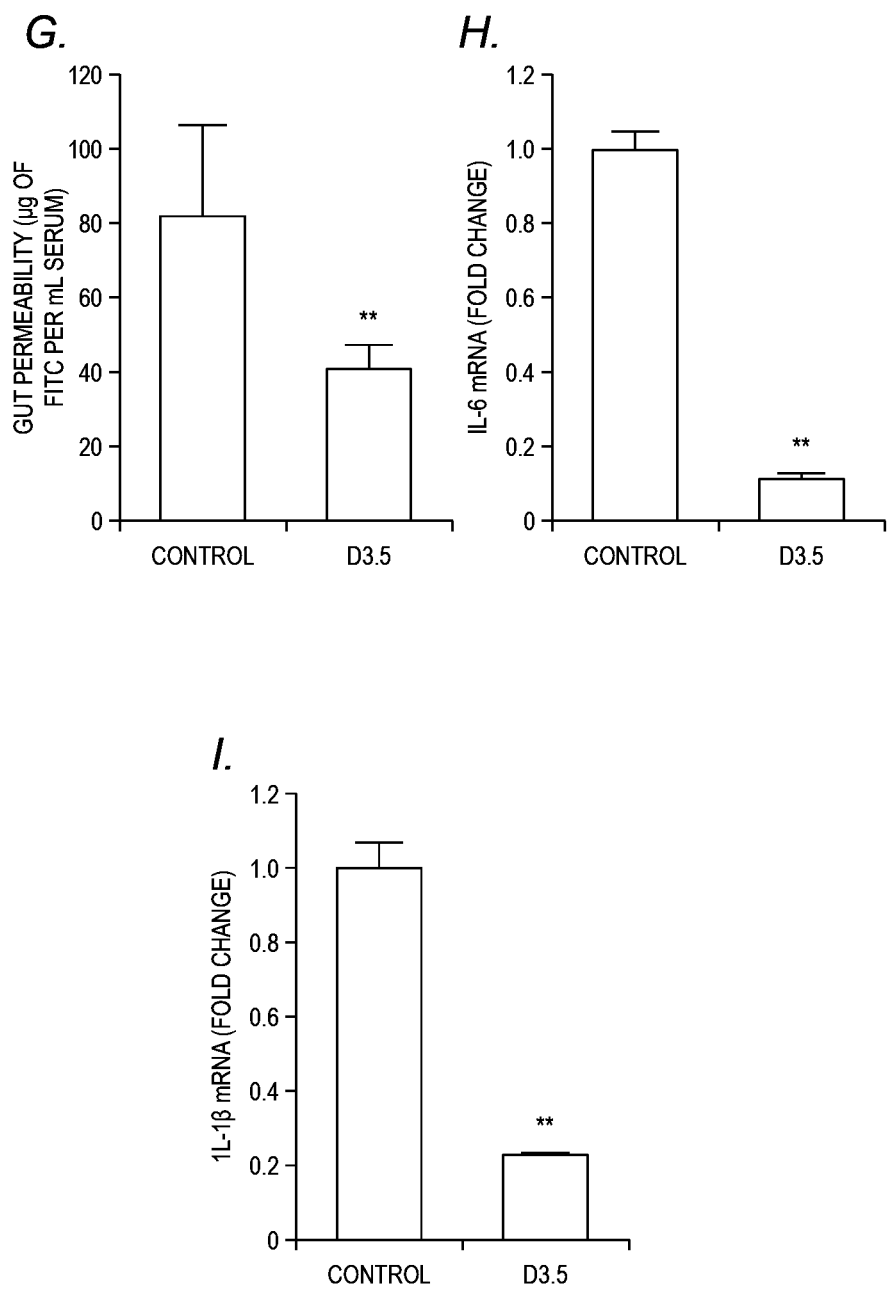

3. D3.5 improved physical and cognitive functions, with reduced leaky gut and inflammation in older obese mice. Obese older adults commonly have decline in their physical function (motility), increased anxiety and decreased cognition (learning and memory) (Dahl et al. 2012; DeJesus et al. 2016; Virta et al. 2013), and we tested the effects of D3.5 feeding on these ailments in older HFD-fed mice. We found that the older mice fed with D3.5 maintained better physical function in terms of increased total motor activity (indicator of walking) compared to their age and gender matched controls (FIG. 2, panels A and B). In addition, other physical function indicators like hanging time on inclined screen (a measure of muscle strength) was significantly higher in D3.5 fed older mice (FIG. 2, panel C). The feeding of D3.5 also significantly decreased anxiety (an another common ailment in older people) (Borta and Schwarting 2005) indicated by decreased rate of rearing (FIG. 2, panel D) and increased time spent in the center during open field test (FIG. 2, panel E). Interestingly, we also found that the D3.5 feeding significantly increased cognitive function in terms of enhanced learning improvements during Morris Water Maze test in older mice compared to their non-treated controls (FIG. 2, panel F). In addition, leaky gut and inflammation are often higher in older adults, and are major risk factors for poor health outcomes in older adults (Borta and Schwarting 2005). Interestingly, we found that the feeding of D3.5 significantly decreased gut permeability (leaky gut) in terms of reduced diffusion of FITC-dextran (3-5 kDa) from gut to the blood (FIG. 2, panel G), that was associated with lower expression of inflammatory genes like IL-6 and IL 1β in the intestine of D3.5 fed older obese mice compared to controls (FIG. 2, panels H and I). These results indicate that the feeding of D3.5 maintained significantly improved physical and cognitive functions and reduced anxiety that were associated with decreased leaky gut and inflammation in older mice.

Figure 3:
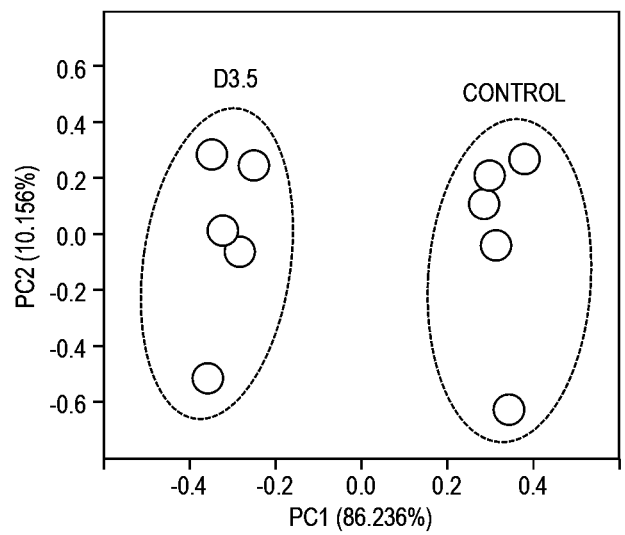
FIG. 3. Effects of D3.5 on gut microbiome after treatment for 8 weeks. (A) Principal coordinate analysis (PCA) showing the β-diversity clustering of gut microbiome from mice (n=6 in each group) fed with D3.5 and the control group. Major changes in bacteria phyla (B), families (C) and genera (D) after treatment with D3.5. (E) Abundance of Akkermansia was significantly increased in the microbiome of older mice from D3.5 group. (F) Cladograms of linear discrimination analysis (LDA) demonstrating clustering of gut microbiome from mice in the D3.5 group in contrast to the control group.
Figure 3:
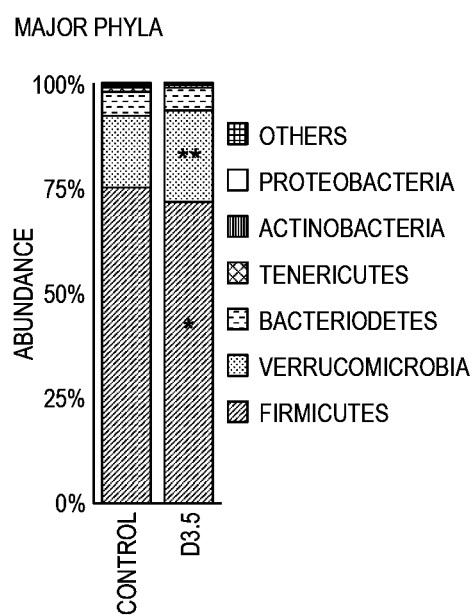
Figure 3:
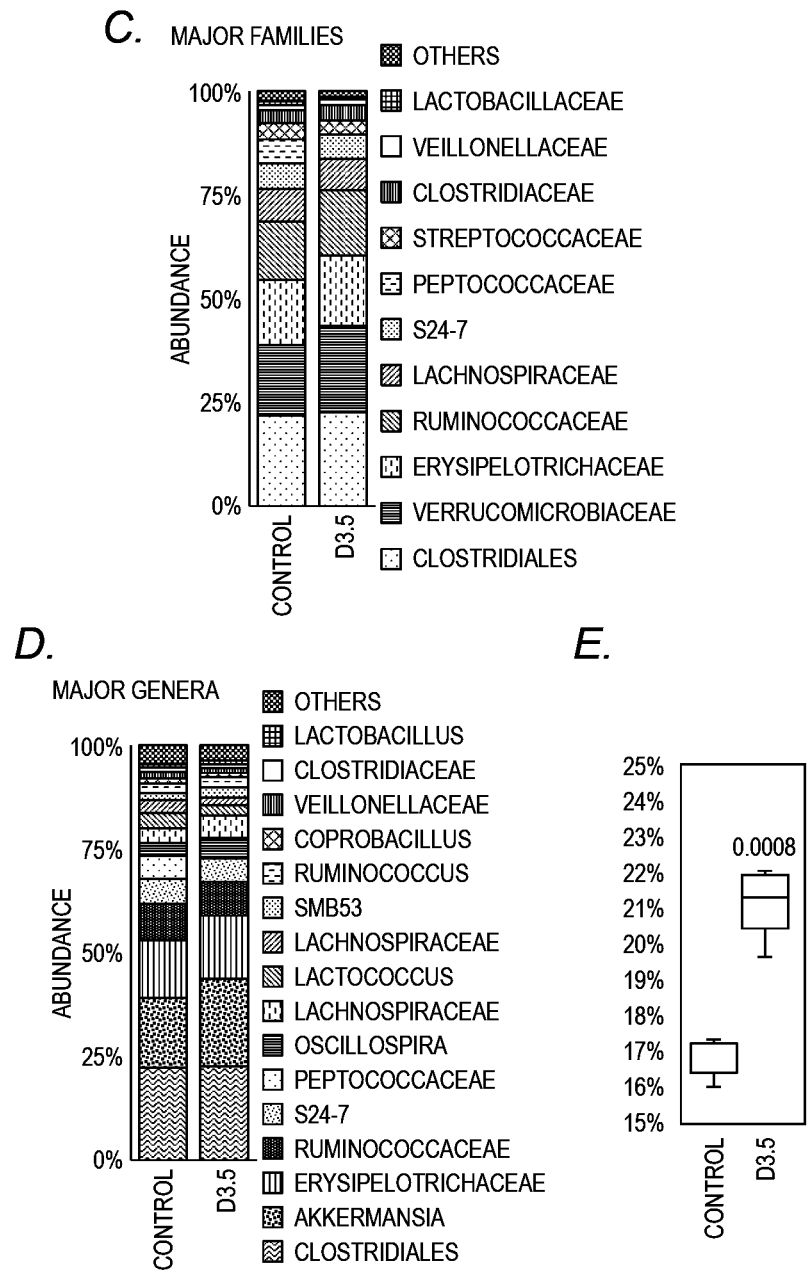
Figure 3:
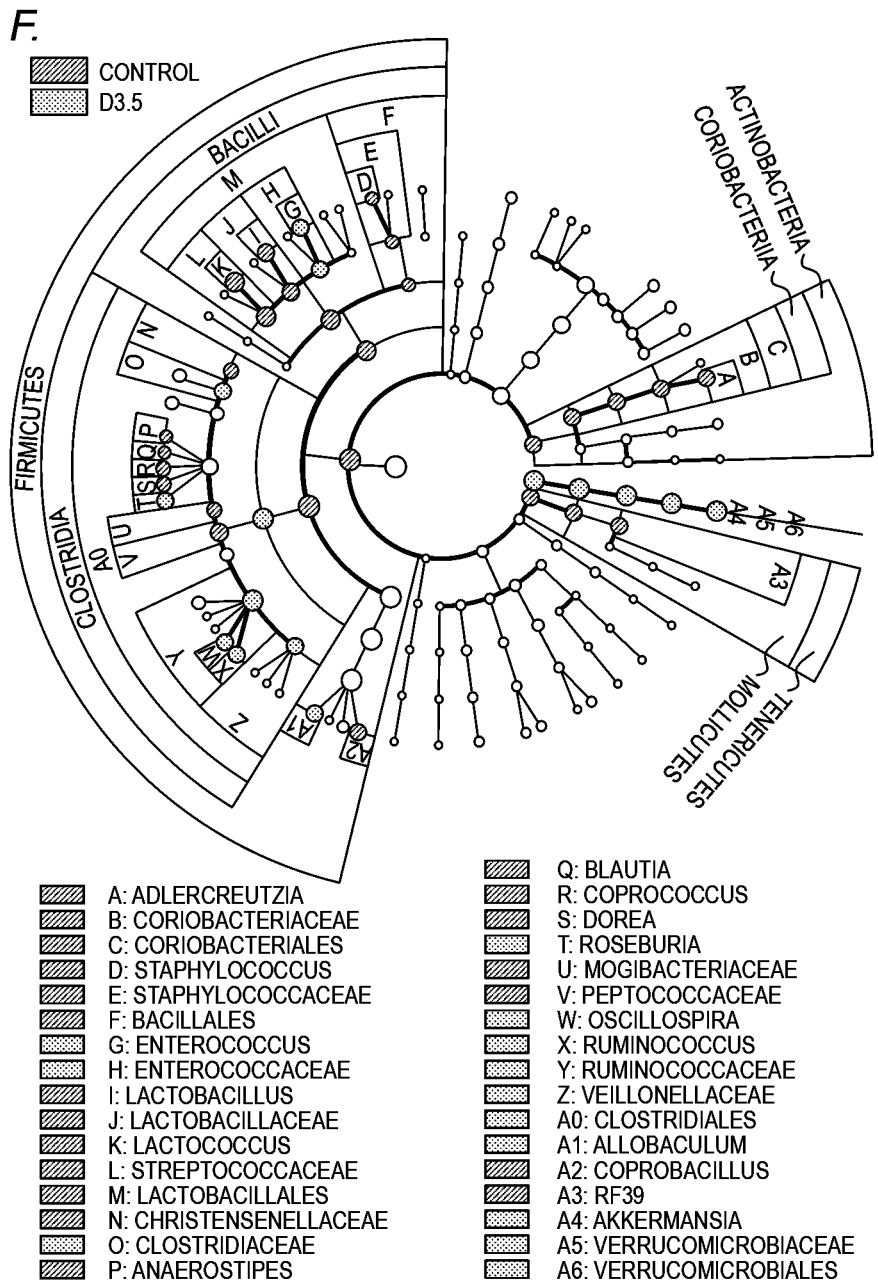

4. D3.5 beneficially modulated gut microbiome in older obese mice. We did not expect the feeding of dead D3.5 to have a major impact on gut microbiome, because of its dead nature. Instead, we found that feeding of D3.5 significantly modulated gut microbiome in older mice (FIG. 3). The gut microbiome signature in terms of β-diversity was dramatically different in D3.5 fed older mice compared to their controls (FIG. 3, panel A), without significant changes in α-diversity indices. However, microbial signatures were distinctly clustered in D3.5 compared to their controls. Further, D3.5 feeding significantly decreased abundance of metabolically detrimental bacterial phyla like Firmicutes, while increasing the abundance of metabolically beneficial bacteria like Verrucomicrobia phyla and Verrucomibiaceae family (FIG. 3, panels B and C). Feeding with D3.5 increased the amounts of Verrucomicrobiaceae, Verrucomicrobiales, Verrucomicrobiae and *Akkermansia* species, while decreased ratios of Actinobacteria, Adlercreutzia, Coriobacteriales and Coriobacteriia (FIG. 3, panels D-F). The common mucin degrading bacteria called *Akkermansia muciniphila* abundance was significantly increased in D3.5-fed older mice compared to their controls (data not shown).

Figure 4:
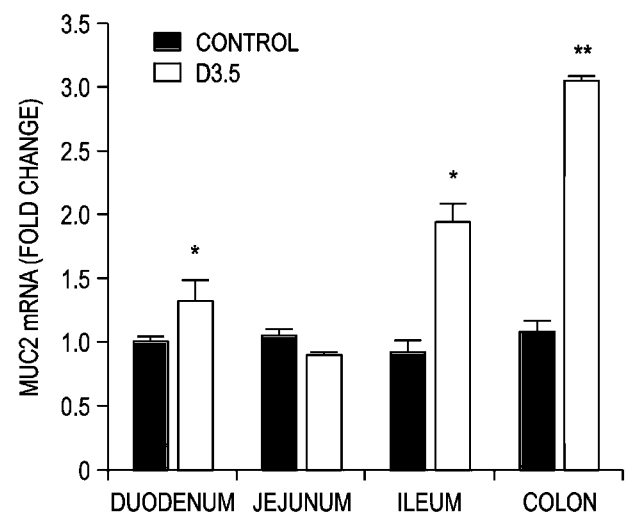
FIG. 4. Muc2 analysis in aged mice and mice after fecal microbiome transplant treatment. (A) Real time PCR results indicated increase of mucin 2 transcription in duodenum, ileum and especially colon from the D3.5 treated mice. (B) Western blotting demonstrated the higher expression of mucin 2 in the colon of mice from the D3.5 group. (C) Comparison of mucin in the feces from D3.5 and the control group (P=0.08). (D) Ileum histology with AB/PAS staining showed higher number of goblet cells in the D3.5 group. Mice transplanted with the microbiome solutions prepared with caecum from the D3.5 group also showed higher mucin 2 transcription as analyzed by real time PCR (E); higher mucin 2 expression indicated with western blotting (F); higher fecal mucin (p=0.13) (G) and more goblet cells in Ileum (H). Data are presented as mean SD. *P<0.05, **P<0.001.
Figure 4:
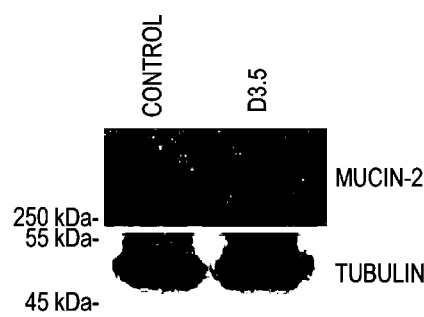
Figure 4:
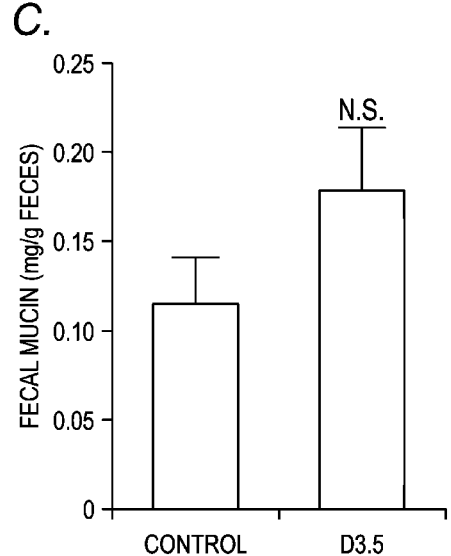
Figure 4:
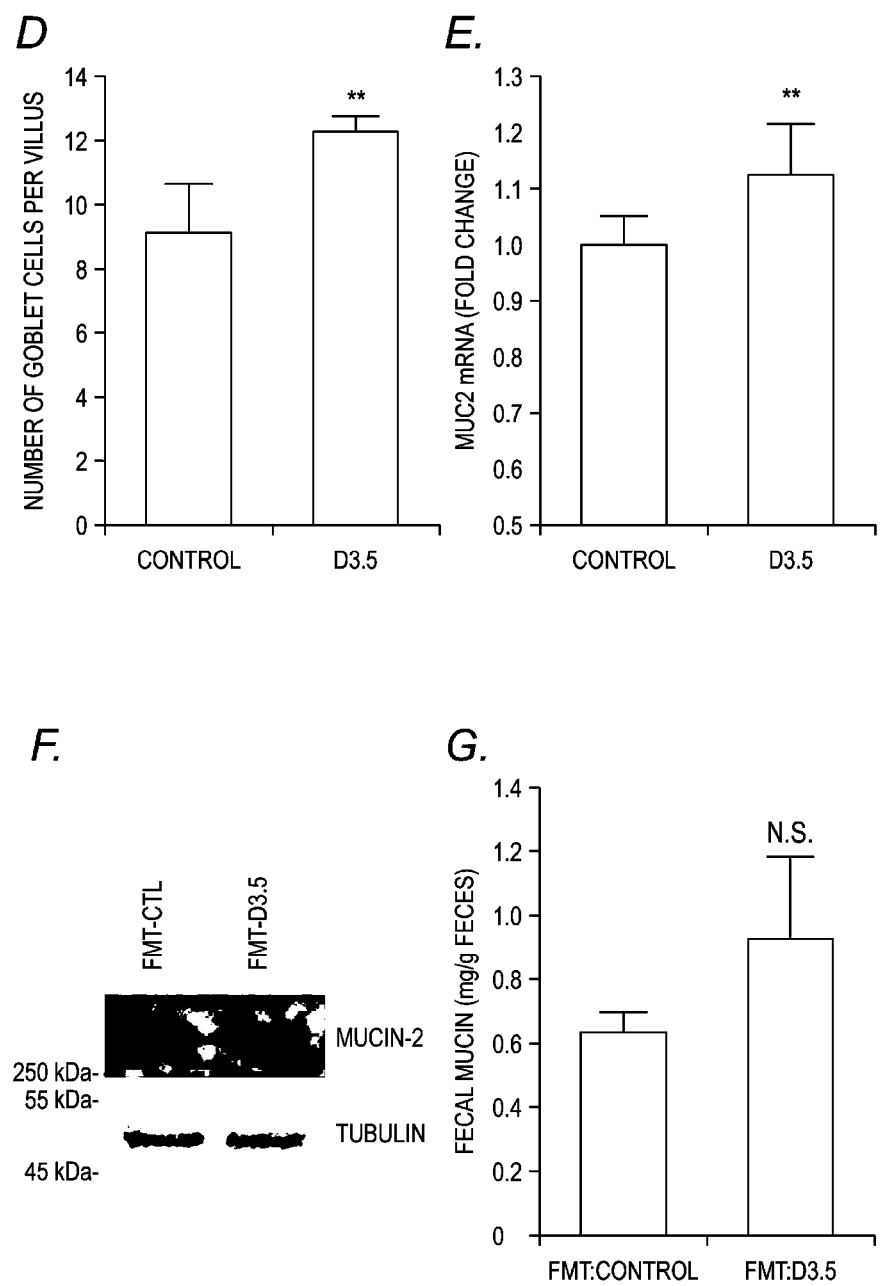
Figure 4:
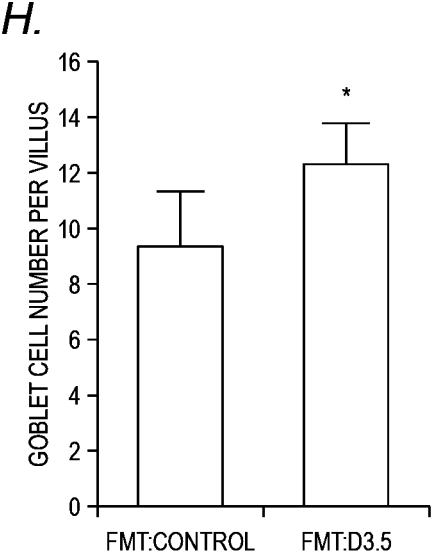

5. D3.5 administration increased mucin production. To explain the dramatic increase of *A. muciniphila* by D3.5, we reasoned that mucin (food source for *A. muciniphila*) (Zhou 2017) levels may have increased in the gut of D3.5-fed older mice, leading to the increased in *A. muciniphila* as a feedback mechanism. Muc2 (a major isoform of mucin abundantly expressed in intestine) expression was significantly increased in duodenum, ileum and colon of D3.5 fed older obese mice compared to their controls (FIG. 4, panel A). D3.5 feeding also significantly increased the expression of mucin protein in colon along with increased mucin secretion in the feces compared to their controls (FIG. 4, panels B and C). Mucin is secreted from goblet cells, (Pelaseyed et al. 2014) and the goblet cell mass was significantly higher (34.6%) in D3.5 fed mice compared to their non-treated controls (FIG. 4, panel D), suggesting that the observed increase in mucin production could be explained by a larger goblet cell mass.

To further explore whether D3.5 modulated changes in the gut microbiome contribute in modulation of goblet cell and mucin biology, we transplanted gut microbiome from D3.5 fed (FMT-D3.5) and their control mice (FMT-Control) to gut cleaned (GC; using antibiotics and poly ethylene glycol [PEG] protocol) mice. (Wrzosek et al. 2018b) Muc2 mRNA and mucin protein as well as goblet cell mass were significantly increased in the gut of FMT-D3.5 recipient GC mice compared to FMT-control recipient GC mice (FIG. 4, panels E-H). These results indicate that D3.5 feeding modulated gut microbiome contributes in promoting goblet cell mass and mucin production.

Figure 5:
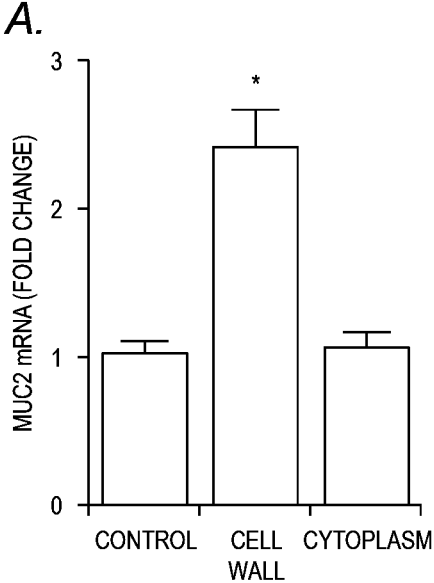
FIG. 5. Mucin analysis in cells after treatment with different D3.5 components. (A) Real time PCR exhibited higher mucin 2 transcription was detected in cells treated with cell wall compared with that treated with cytoplasm. (B) Increased mucin 2 transcription was detected in cells treated with LTA, while PGN-WTA decreased transcription of mucin 2. Data are presented as mean±SD. *P<0.05, **P<0.001.
Figure 5:
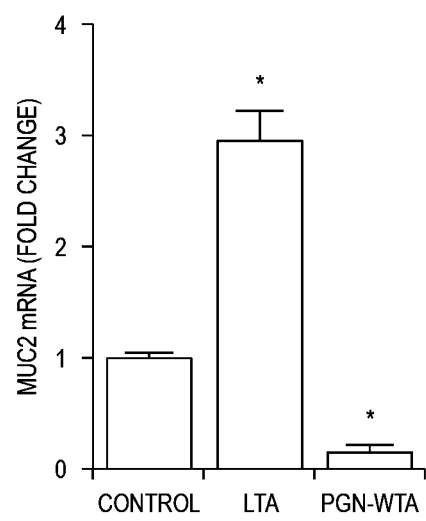

6. Lipoteichoic acid (LTA) derived from the cell wall of D3.5 increases mucin production. In order to discover the specific cellular components of dead D3.5 which enhance the mucin production, we first fractionated cell wall and cytoplasmic components, and subsequently treated CMT93 cells (a mouse goblet cell line) with these components. Muc2 mRNA expression and mucin content (labelled with PAS staining) were increased only in the cell wall fraction of D3.5-treated cells (FIG. 5, panel A). To further determine which D3.5 cell wall constituents that enhanced mucin production, we fractionated the D3.5 cell wall into the peptidoglycan and LTA fractions, and found that the LTA fraction-treated CMT93 goblet cells exhibited significantly higher expression of Muc2 mRNA and mucin/PAS staining, suggesting that the LTA from the D3.5 cell wall activates mucin production from goblet cells (FIG. 5, panel B).

Figure 6:
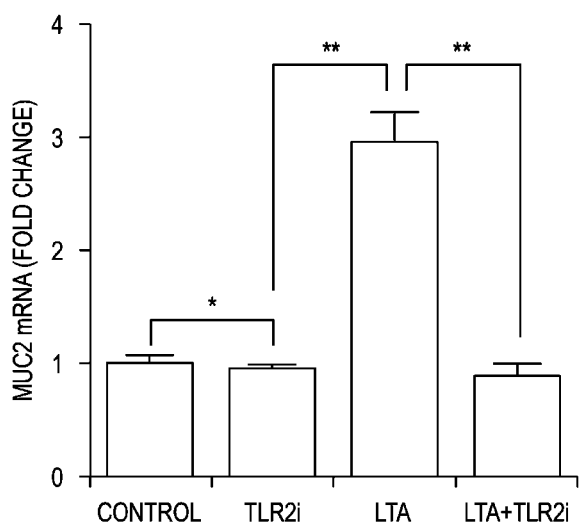
FIG. 6. Mucin analysis in cells treated with TLR inhibitor and TLR2 knockout mice. (A) transcription analysis of mucin 2 with real time PCR. Control, cells treated with water; TLRi, cells treated with water plus TLR2 inhibitor (CU CPT22); LTA, cells treated with 200 μg/ml LTA; LTA+TLR2i, cells treated with both LTA and CU CPT22. (B) Comparison of mucin 2 expression in colon from C57BL/6J and TLR2 KO mice with western blotting. Control, C57BL/6J mice fed with water; D3.5, C57BL/6J mice fed with dead L. paracasei D3.5; LTA, C57BL/6J mice fed with LTA extracted from L. paracasei D3.5; TLR2 KO-CTL, TLR 2 knockout mice fed with water; TLR2 KO-D3.5, TLR2 knockout mice fed with dead L. paracasei D3.5; TLR2 KO-LTA, TLR2 knockout mice fed with LTA from D3.5. (C) Goblet cell counting from C57BL/6J mice fed with water (control), dead L. paracasei D3.5 and LTA from L. paracasei D3.5 (LTA) with AB/PAS staining. (D) Goblet cell counting from TLR2 knockout mice fed with water (control), dead L. paracasei D3.5 and LTA from D3.5 (LTA) with AB/PAS staining. Data are presented as mean±SD. *P<0.05, **P<0.001.
Figure 6:
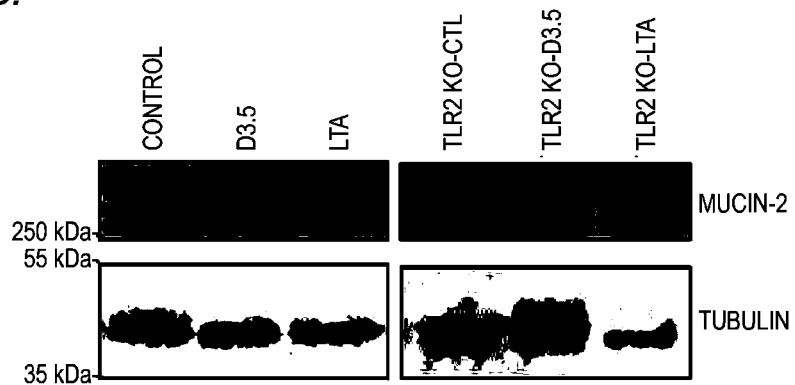
Figure 6:
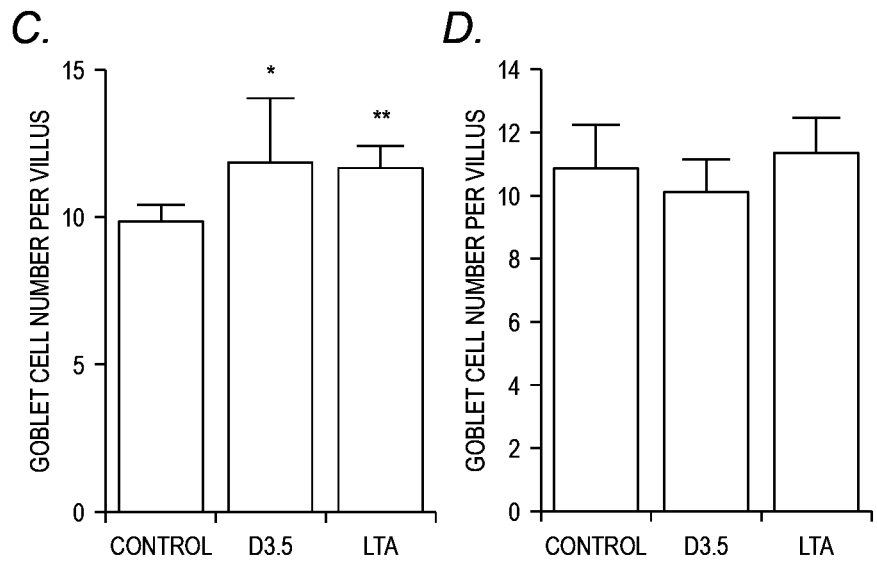

7. LTA activates TLR-2/p38-MAPK signaling to promote Muc2 expression and suppress NFκB to reduce inflammation. To further establish how LTA increases Muc2 expression and mucin production, considering that Gram-positive bacterial components stimulate toll like receptor-2 (TLR-2) signaling, (Hong et al. 2014; Kim et al. 2014; Schwandner et al. 1999; Travassos et al. 2004) we hypothesized that LTA activates the TLR2 signaling and enhances Muc2 expression in intestinal goblet cells. LTA treatment stimulated increase in Muc2 mRNA in the CMT93 cells was significantly abolished in the presence of TLR2 inhibitor (CU CPT22) (FIG. 6, panel A), suggesting that TLR2 signaling mediates the effects of LTA to enhance the expression of Muc2 in CMT93 goblet cells. In addition, oral administration of D3.5 and its cell wall derived LTA for 1 week significantly increased Muc2 expression as well as enhanced goblet cell mass in the mouse gut, however, such effects of D3.5 and its cell wall LTA failed in TLR2 knockout (KO) mice (FIG. 6, panels B-D), further indicating that LTA required TLR2 signaling activation to enhance goblet cell mass and mucin production.

LTA also significantly reduced the inflammatory markers like IL-6, IL-1β and TNF-α in the intestine of C57BL/6J mice (FIG. 7, panels A-C), however, these effects were not seen in the TLR2 KO mice (FIG. 7, panels D-F), suggesting that LTA-reduced inflammation also depends on intact TLR2 signaling. These results suggesting that LTA stimulates TLR2 signaling to enhance goblet cell mass and mucin production, which in turn reduced leaky gut and intestinal inflammation.

Figure 7:
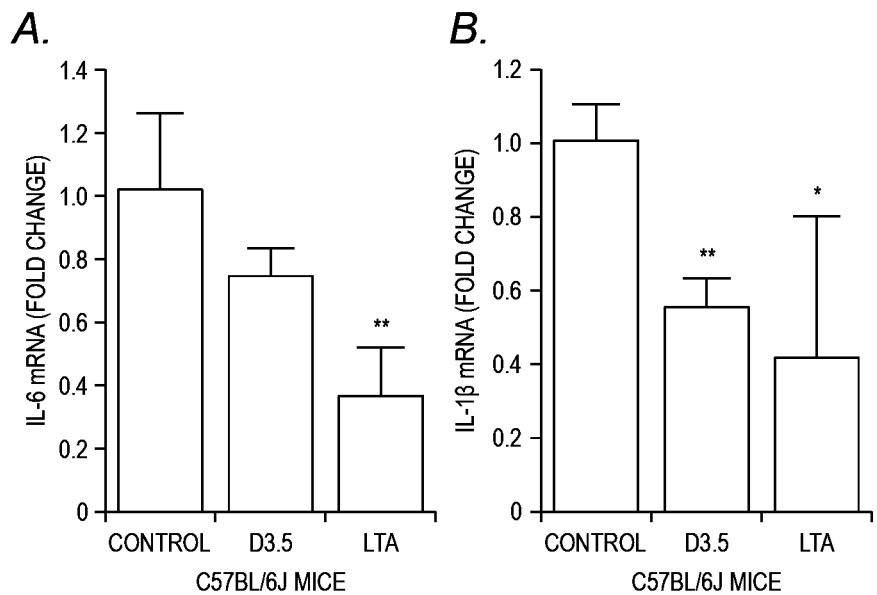
FIG. 7. Immune factors detection through real time PCR and expression difference of proteins involved in TLR2 pathway. Transcription comparison of IL-6 (A), IL-1β (B) and TNFα (C) in C57BL/6J mice treated with water (control), dead L. paracasei D3.5 and LTA from D3.5 (LTA). Determination of IL-6 (D), IL-1β (E) and TNFα (F) in TLR2 knockout mice treated with water (control), dead L. paracasei D3.5 and LTA from D3.5 (LTA). (G) Western blotting analysis for proteins (Phospho-p38-MAPK, P38-MAPK, Phospho-JNK, JNK, NFkB) included in TLR2 pathway as well as the control protein tubulin. Older mice was fed with water (control) and dead L. paracasei D3.5 for 16 weeks; For C57BL/6J mice and TLR2 knockout mice, water, dead L. paracasei D3.5 and LTA from D3.5 were given to the CTL, D3.5 and LTA groups, respectively for 5 days. Data are presented as mean±SD. *P<0.05, **P<0.001.
Figure 7:
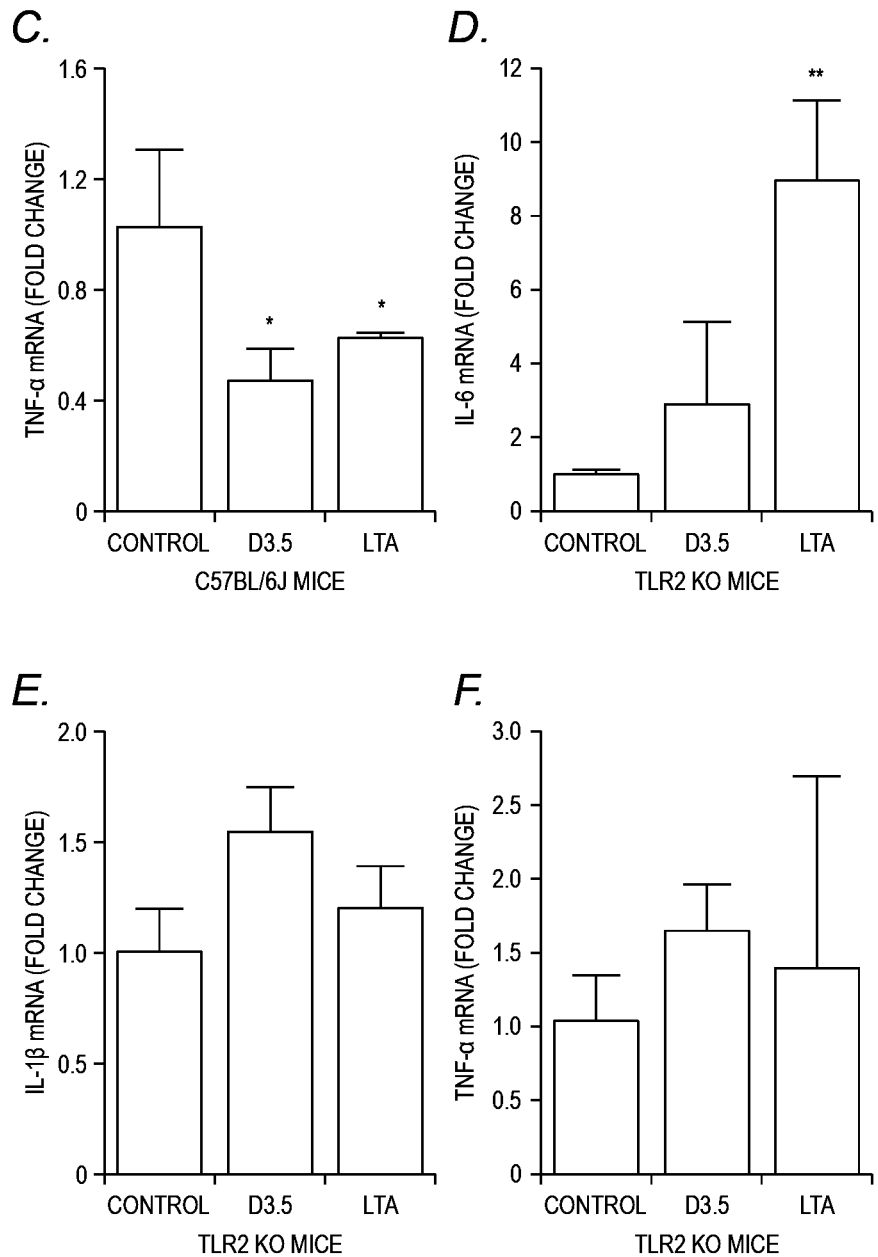
Figure 7:
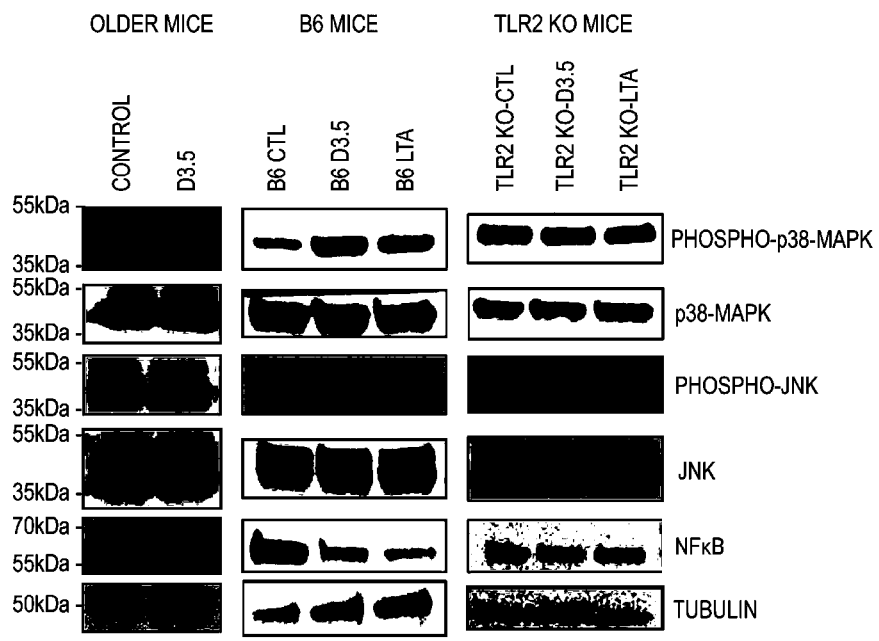

To further discover which signaling mediators of the TLR2 pathway participate in response to LTA, we found that the levels of phosphorylated p38 MAPK proteins were significantly increased in the intestines of both old and young C57BL/6J mice, while this activation was abolished in TLR2 KO mice (FIG. 7, panel G). However, total p38 MAPK as well as phospho- and total-JNK proteins did not significantly change upon LTA treatment, suggesting that p38-MAPK is activated downstream of TLR2, without impacting JNK signaling (FIG. 7, panel G). The protein levels of NF-κB, a master regulator of inflammatory pathways, was significantly decreased in LTA-treated wild-type mice, but not in TLR2 KO mice (FIG. 7, panel G). Together, these data show that LTA activation of TLR2-p38 MAPK signaling enhanced mucin production, suppressed NF-κB signaling and reduced inflammatory cytokines.

DISCUSSION

Increasing prevalence of age-related ailments like decline in physical and cognitive functions, obesity, diabetes, cardiovascular diseases and cancer are significantly associated with gut microbiome dysbiosis, leaky gut and inflammation. (Buford 2017; Nagpal et al. 2018a; Shimizu 2018) Herein, we demonstrated that a dead probiotic strain *L. paracasei* D3.5 isolated from infant gut enhanced life-span and maintained better physical function and muscle mass in *C. elegans* and prevented HFD-induced metabolic dysfunctions, leaky gut and inflammation in older mice. Mechanistically, D3.5 cell wall derived LTA enhances goblet cells and mucin production by activating TLR2-p38 MAPK signaling and reducing inflammation by inhibiting NFκB resulting in decreased expression of the pro-inflammatory cytokines IL-6, IL-1β and TNF-α.

Although the precise mechanisms of increased inflammation in older adults are elusive, increased gut epithelial permeability in patients presenting leaky gut is common in older adults and can serve as a major trigger for intestinal and systemic inflammation. (Stehle Jr et al. 2012) Emerging evidence indicates that gut microbiome dysbiosis is associated with poor health outcomes in older adults and may contribute in development of leaky gut and inflammation. (Nagpal et al. 2018a) The abundance of detrimental bacteria like Gram-negative bacteria are often increased in the older gut, (Schiffrin et al. 2010) elevating the levels of pro-inflammatory molecules like LPS (Lipopolysaccharide), an endotoxin and major constituent of Gram-negative bacterial cell wall. LPS can diffuse in leaky gut conditions, causing endotoxemia and inflammation in local tissues as well as systemic inflammation (Mu et al. 2017). Therefore, gut microbiome modulators that are able to: (i) reduce abundance of Gram-negative bacteria and (ii) improve gut barrier integrity like thickening mucus layer and increasing tight junctions, could reduce leaky gut and inflammation. (Kelly et al. 2015) Probiotics can be ideal candidates for this purpose because these are mostly Gram-positive and therefore can balance the growth of Gram-negative bacteria in older gut, thereby reducing LPS load and the inflammation.

In addition, certain strains of probiotics have been shown to induce mucin production. For example, bifidobacteria increase mucus production and protect from HFD-induced microbiota dysbiosis and obesity, (Schroeder et al. 2018) and *Lactobacillus* GG upregulates Muc2 gene expression in intestinal epithelial cells. (Wang et al. 2015) However, the impact of probiotics in age-related leaky gut, inflammation and mucin biology remains elusive. Also, probiotics are known for their beneficial effects in several human diseases including diabetes, obesity, Cardiovascular diseases and cancer, (Azad et al. 2018; Landete et al. 2017) but their impact on longevity is not well defined. In this study, we demonstrated that only a few selected human-origin probiotic strains exhibit beneficial effects in extending the lifespan of *C. elegans*. Among the six selected probiotic strains, (Nagpal et al. 2018b) only two strains of lactobacilli like *L. plantarum* SK9 and *L. paracasei* D3.5 fed *C. elegans* show beneficial effects to extend life-span. D3.5 feeding showed the highest extension in life-span and hence was selected for further studies. These results indicate that not all probiotics have anti-aging effects, indeed these effects remain very strain specific. Interestingly, D3.5 feeding also enhanced physical function and maintained higher muscle mass in *C. elegans*, suggesting that the probiotic D3.5 prevented aging-related muscle mass decline. The *C. elegans* longevity assay protocols require addition of antibiotics and antifungal to prevent contamination of the worm media. Thus, probiotics fed to *C. elegans* were dead. That led us to discover that the dead D3.5 has anti-aging effects, increasing life-span of *C. elegans* and preserving muscle mass and physical functions. Overall, these findings are unusually significant in several ways: (i) they establish a new paradigm that dead probiotics can also have beneficial effects, in contrary to the old paradigm suggesting probiotic are needed to be alive to exhibit beneficial effects; (ii) dead probiotics eliminate the risk of leaking live bacteria systemically in patients with severe leaky gut, thus increasing the risk of bacteremia/sepsis; and (iii) dead probiotics may offer an advantage for food industry applications as they can easily be supplemented in several food lines/products not amenable for live probiotics, such as beverages, baked products and others.

Obesity and metabolic dysfunctions are common in older adults with poor health outcomes, and HFD-feeding induces these ailments much faster in older mice compared to younger ones. (Dominguez and Barbagallo 2016; Nunes-Souza et al. 2016) We found that D3.5 feeding to older mice prevented the HFD-induced glucose intolerance, insulin resistance, hepatic steatosis (lipid accumulation in liver), and low-grade inflammation in adipose tissue. D3.5-fed older mice maintained better physical and cognitive functions, with reduced leaky gut and inflammation, indicating that the anti-aging effects observed with D3.5 in *C. elegans* were translated to mammals, like older obese mice. Intriguingly, we found that the D3.5 also significantly modulated gut microbiome composition in these older obese mice, as it considerably enhanced the abundance of the mucin degrading bacteria *A. muciniphila*. Indeed, *A. muciniphila* is known to have beneficial effects against obesity, diabetes (Dao et al. 2016; Everard et al. 2013) and other human diseases along with anti-inflammatory effects. (Naito et al. 2018; Ottman et al. 2017) We posited that the increased abundance of *A. muciniphila* might be due to increased mucin production in the gut of D3.5 fed mice. Because mucin is a major food source for *A. muciniphila*, increased mucin production may sustain growth of this bacteria. Interestingly enough, the intestine of D3.5 fed mice had significantly increased mucin production along with higher Muc2 expression and goblet cells mass. The fecal microbiome transplantation studies demonstrated that the D3.5 modulated gut microbiome enhances goblet cell mass and mucin production. However, these changes might be due to the presence of D3.5 and its cellular ingredients in the donor feces which might have been transferred to the recipient mice gut and showing these residual effects.

Using biochemical fractionation, we demonstrated that the D3.5's cell wall-derived LTA is the key component responsible for enhancing Muc2 expression and mucin production from goblet cells. LTA has been known to promote goblet cell function in other systems too, (Nell et al. 2004) supporting our data showing that LTA from D3.5 probiotics can promote mucus thickness, which can reduce pathogenic bacteria invasion and leakiness. We further investigated the mechanism(s) by which LTA can stimulate goblet cells to produce mucin. We also found that LTA action depends on TLR2 signaling to induce Muc2 expression, in agreement with the fact that the Gram-positive bacteria commonly activate TLR2 signaling. (Hanzelmann et al. 2016; Ninkovic et al. 2016) Activation of TLR2 signaling further recruit and initiate downstream signaling cascade by phosphorylation of p38 MAPK. (Kawai and Akira 2010; Ribeiro et al. 2010) Accordingly, D3.5 and LTA treatment increased phospho-p38-MAPK levels in the mouse intestine, indicating that LTA activates TLR2 and p38-MAPK signaling, which in turn increases Muc2 expression and goblet cell mass. Interestingly, our results also demonstrated that NF-κB protein levels were significantly decreased. Suppression of NF-κB signaling is known to diminish the expression of proinflammatory cytokines such as IL-6, IL-1β and TNF-α. (Tak and Firestein 2001) Thus, our results indicate that LTA downregulates NFκ-B-mediated proinflammatory responses in the intestinal tissue milieu. Altogether, our results demonstrated that a newly isolated human-origin probiotic strain D3.5 is beneficial to enhance longevity and ameliorate aging-related health ailments like metabolic dysfunctions, leaky gut and inflammation. D3.5 cell wall-derived LTA activated TLR2-p38 MAPK signaling to promote Muc2 expression and mucin production from goblet cells to reduce leaky gut and suppress NFκB signaling to reduce inflammation. These results demonstrated that the D3.5 and its cell wall derived LTA could be used as a biotherapy to prevent and/or treat age-related gut microbiome dysbiosis, leaky gut and inflammation in the older adults.

REFERENCES

Azad M A K, Sarker M, Li T, Yin J (2018) Probiotic Species in the Modulation of Gut Microbiota: An Overview Biomed Res Int 2018:9478630 doi:10.1155/2018/9478630

Bahitham W, Watts R, Nelson R, Lian J, Lehner R (2016) Liver-specific expression of carboxylesterase 1 g/esterase-x reduces hepatic steatosis, counteracts dyslipidemia and improves insulin signaling Biochim Biophys Acta 1861:482-490 doi:10.1016/j.bbalip.2016.03.009

Borta A, Schwarting RKW (2005) Inhibitory avoidance, pain reactivity, and plus-maze behavior in Wistar rats with high versus low rearing activity Physiology & Behavior 84:387-396 doi:10.1016/j.physbeh.2005.01.009

Buford T W (2017) (Dis)Trust your gut: the gut microbiome in age-related inflammation, health, and disease Microbiome 5:80 doi:10.1186/s40168-017-0296-0

Cani P D, Bibiloni R, Knauf C, Waget A, Neyrinck A M, Delzenne N M, Burcelin R (2008) Changes in Gut Microbiota Control Metabolic Endotoxemia-Induced Inflammation in High-Fat Diet-Induced Obesity and Diabetes in Mice Diabetes 57:1470-1481 doi:10.2337/db07-1403

Caporaso J G et al. (2010) QIIME E allows analysis of high-throughput community sequencing data Nat Methods 7:335-336 doi:10.1038/nmeth.f.303

Crowther R S, Wetmore R F (1987) Fluorometric assay of O-linked glycoproteins by reaction with 2-cyanoacetamide Anal Biochem 163:170-174 doi:10.1016/0003-2697(87)90108-4

Dahl A K, Hassing L B, Fransson E I, Gatz M, Reynolds C A, Pedersen N L (2012) Body mass index across midlife and cognitive change in late life International Journal of Obesity 37:296-302 doi:10.1038/ijo.2012.37

Dao M C et al. (2016) *Akkermansia muciniphila* and improved metabolic health during a dietary intervention in obesity: relationship with gut microbiome richness and ecology Gut 65:426-436 doi:10.1136/gutjnl-2014-308778

DeJesus R S et al. (2016) Associations between anxiety disorder diagnoses and body mass index differ by age, sex and race: a population based study 12:67

Dominguez L J, Barbagallo M (2016) The biology of the metabolic syndrome and aging Curr Opin Clin Nutr Metab Care 19:5-11 doi:10.1097/MCO.0000000000000243

Everard A et al. (2013) Cross-talk between *Akkermansia muciniphila* and intestinal epithelium controls diet-induced obesity Proc Natl Acad Sci USA 110:9066-9071 doi:10.1073/pnas.1219451110

Gaffney C J, Bass J J, Barran T F, Szewczyk N J (2014) Methods to assess subcellular compartments of muscle in *C. elegans* J Vis Exp:e52043 doi:10.3791/52043

Hanzelmann D et al. (2016) Toll-like receptor 2 activation depends on lipopeptide shedding by bacterial surfactants Nat Commun 7:12304 doi:10.1038/ncomms12304

Heß N et al. (2017) Lipoteichoic acid deficiency permits normal growth but impairs virulence of *Streptococcus pneumoniae* 8:2093

Hong S W, Baik J E, Kang S S, Yun C H, Seo D G, Han S H (2014) Lipoteichoic acid of *Streptococcus mutans* interacts with Toll-like receptor 2 through the lipid moiety for induction of inflammatory mediators in murine macrophages Mol Immunol 57:284-291 doi:10.1016/j.molimm.2013.10.004

Kawai T, Akira S (2010) The role of pattern-recognition receptors in innate immunity: update on Toll-like receptors Nat Immunol 11:373-384 doi:10.1038/ni.1863

Kelly J R, Kennedy P J, Cryan J F, Dinan T G, Clarke G, Hyland N P (2015) Breaking down the barriers: the gut microbiome, intestinal permeability and stress-related psychiatric disorders Front Cell Neurosci 9:392 doi:10.3389/fncel.2015.00392

Kim H, Jung B J, Jeong J, Chun H, Chung D K (2014) Lipoteichoic acid from *Lactobacillus plantarum* inhibits the expression of platelet-activating factor receptor induced by *Staphylococcus aureus* lipoteichoic acid or *Escherichia coli* lipopolysaccharide in human monocyte-like cells J Microbiol Biotechnol 24:1051-1058

Kim J Y, Woo H J, Kim K H, Kim E-R, Jung H-K, Juhn H-N, Lee H J J J M B (2002) Antitumor activity of *Lactobacillus plantarum* cytoplasm on teratocarcinoma-bearing mice 12:998-1001

Landete J M, Gaya P, Rodriguez E, Langa S, Peiroten A, Medina M, Argues J L (2017) Probiotic Bacteria for Healthier Aging: Immunomodulation and Metabolism of Phytoestrogens Biomed Res Int 2017:5939818 doi:10.1155/2017/5939818

Mu Q, Kirby J, Reilly C M, Luo X M (2017) Leaky Gut As a Danger Signal for Autoimmune Diseases Front Immunol 8:598 doi:10.3389/fimmu.2017.00598

Nagpal R et al. (2018a) Gut microbiome and aging: Physiological and mechanistic insights Nutr Healthy Aging 4:267-285 doi:10.3233/NHA-170030

Nagpal R et al. (2018b) Human-origin probiotic cocktail increases short-chain fatty acid production via modulation of mice and human gut microbiome Sci Rep 8:12649 doi:10.1038/s41598-018-30114-4

Naito Y, Uchiyama K, Takagi T (2018) A next-generation beneficial microbe: *Akkermansia muciniphila* J Clin Biochem Nutr 63:33-35 doi:10.3164/jcbn.18-57

Nell M J, Tjabringa G S, Vonk M J, Hiemstra P S, Grote J J (2004) Bacterial products increase expression of the human cathelicidin hCAP-18/LL-37 in cultured human sinus epithelial cells FEMS Immunol Med Microbiol 42:225-231 doi:10.1016/j.femsim.2004.05.013

Ninkovic J et al. (2016) Differential effects of gram-positive and gram-negative bacterial products on morphine induced inhibition of phagocytosis Sci Rep 6:21094 doi:10.1038/srep21094

Nunes-Souza V, Cesar-Gomes C J, Da Fonseca L J, Guedes Gda S, Smaniotto S, Rabelo L A (2016) Aging Increases Susceptibility to High Fat Diet-Induced Metabolic Syndrome in C57B L/6 Mice: Improvement in Glycemic and Lipid Profile after Antioxidant Therapy Oxid Med Cell Longev 2016:1987960 doi:10.1155/2016/1987960

Nunez J (2008) Morris Water Maze Experiment J Vis Exp doi:10.3791/897

Ottman N et al. (2017) Pili-like proteins of *Akkermansia muciniphila* modulate host immune responses and gut barrier function PLoS One 12:e0173004 doi:10.1371/journal.pone.0173004

Pelaseyed T et al. (2014) The mucus and mucins of the goblet cells and enterocytes provide the first defense line of the gastrointestinal tract and interact with the immune system Immunol Rev 260:8-20 doi:10.1111/imr.12182

Ribeiro C M, Hermsen T, Taverne-Thiele A J, Savelkoul H F, Wiegertjes G F (2010) Evolution of recognition of ligands from Gram-positive bacteria: similarities and differences in the TLR2-mediated response between mammalian vertebrates and teleost fish J Immunol 184:2355-2368 doi:10.4049/jimmunol.0900990

Schiffrin E J, Morley J E, Donnet-Hughes A, Guigoz Y (2010) The inflammatory status of the elderly: the intestinal contribution Mutat Res 690:50-56 doi:10.1016/j.mrfmmm.2009.07.011

Schroeder B O, Birchenough G M H, Stahiman M, Arike L, Johansson M E V, Hansson G C, Backhed F (2018) Bifidobacteria or Fiber Protects against Diet-Induced Microbiota-Mediated Colonic Mucus Deterioration Cell Host Microbe 23:27-40 e27 doi:10.1016/j.chom.2017.11.004

Schwandner R, Dziarski R, Wesche H, Rothe M, Kirschning C J (1999) Peptidoglycan- and lipoteichoic acid-induced cell activation is mediated by toll-like receptor 2 J Biol Chem 274:17406-17409 doi:10.1074/jbc.274.25.17406

Sedor F A, Holleman C M, Heyden S, Schneider K A (1988) Reflotron cholesterol measurement evaluated as a screening technique Clin Chem 34:2542-2545

Shimizu Y (2018) Gut microbiota in common elderly diseases affecting activities of daily living World J Gastroenterol 24:4750-4758 doi:10.3748/wjg.v24.i42.4750

Solis G M, Petrascheck M (2011) Measuring *Caenorhabditis elegans* life span in 96 well microtiter plates J Vis Exp doi:10.3791/2496

Stehle Jr J R, Leng X, Kitzman D W, Nicklas B J, Kritchevsky S B, High K P (2012) Lipopolysaccharide-binding protein, a surrogate marker of microbial translocation, is associated with physical function in healthy older adults Journals of Gerontology Series A: Biomedical Sciences and Medical Sciences 67:1212-1218

Tak P P, Firestein G S (2001) NF-kappaB: a key role in inflammatory diseases J Clin Invest 107:7-11 doi:10.1172/JCI11830

Travassos L H, Girardin S E, Philpott D J, Blanot D, Nahori M A, Werts C, Boneca I G (2004) Toll-like receptor 2-dependent bacterial sensing does not occur via peptidoglycan recognition EMBO Rep 5:1000-1006 doi:10.1038/sj.embor.7400248

Virta J J, Heikkila K, Perola M, Koskenvuo M, Raiha I, Rinne J O, Kaprio J (2013) Midlife cardiovascular risk factors and late cognitive impairment European Journal of Epidemiology 28:405-416 doi:10.1007/s10654-013-9794-y Wang Y M, Ge X Z, Wang W Q, Wang T, Cao H L, Wang B L, Wang B M (2015) *Lactobacillus rhamnosus* G G supernatant upregulates serotonin transporter expression in intestinal epithelial cells and mice intestinal tissues Neurogastroenterol Motil 27:1239-1248 doi:10.1111/nmo.12615

Wrzosek L et al. (2018a) Transplantation of human microbiota into conventional mice durably reshapes the gut microbiota 8:6854

Wrzosek L et al. (2018b) Transplantation of human microbiota into conventional mice durably reshapes the gut microbiota Sci Rep 8:6854 doi:10.1038/s41598-018-25300-3

Yadav H, Lee J H, Lloyd J, Walter P, Rane S G (2013) Beneficial metabolic effects of a probiotic via butyrate-induced GLP-1 hormone secretion J Biol Chem 288:25088-25097 doi:10.1074/jbc.M113.452516

Yadav H et al. (2011) Protection from obesity and diabetes by blockade of TGF-beta/Smad3 signaling Cell Metab 14:67-79 doi:10.1016/j.cmet.2011.04.013

Yemitan O, Salandeen H J F (2005) Neurosedative and muscle relaxant activities of aqueous extract of *Bryophyllum pinnatum* 76:187-193

Zhou K (2017) Strategies to promote abundance of *Akkermansia muciniphila*, an emerging probiotics in the gut, evidence from dietary intervention studies J Funct Foods 33:194-201 doi:10.1016/j.jff.2017.03.045

Example 2: Genomic Features of D3.5

We explored the effects of *Lactobacillus* strains including two *Lactobacillus paracasei* (*L. paracasei* D3.5 and *L. paracasei* D10.4) on aging. Surprisingly, *L. paracasei* D3.5 could extend the lifespan of experimental animals like *C. elegans*. Moreover, when fed into older mice, *L. paracasei* D3.5 prevented high fat diet-induced metabolic dysfunction and decreased leaky gut and inflammation. Finally, we found that lipoteichoic acid (LTA) from *L. paracasei* D3.5 was one of the primary factor responsible for these effects. While *L. paracasei* D10.4, even from the same species, showed opposite effects on aging. The results could be due to the fact that two strains of the same species retains different genome and proteome expression profile.

We compared *L. paracasei* D3.5 and *L. paracasei* D10.4 through whole genome and analysis. The whole genome of *L. paracasei* D3.5 and *L. paracasei* D10.4 were sequenced in GENEWIZ, assembled and annotated with two separate pipeline one is a combination of CD-HIT, Augustus, and NRdatabase program while the second is PATRIC program. The sequences genome information is submitted to GenBank database with accession number *L. paracasei* D3.5: JAACXY00000000.1 and *L. paracasei* D10.4: JAAFGQY00000000. Both the genomes were classified in 26 COG functional class in the identified orthogonal sequences with the respective match of genes (FIG. 8).

The whole genome of *L. paracasei* D3.5 contains extra genes contributing to the functional class of E, G, K and S corresponding to Amino acid transport and metabolism, carbohydrate transport and metabolism, coenzyme transport and metabolism and other prediction functions, respectively. Notably, all the reported extra COGs in the strain D3.5 contains the metabolism of specific genes. In the other strain of D10.4, three class of C, D, and L to functional class of energy production and conversion, cell cycle control, cell division, chromosome partitioning and replication, recombination and repair. These results indicate the contribution of more genes of the cell division cycle in strain D10.4 in comparison to strain D3.5.

The foregoing is illustrative of the present invention, and is not to be construed as limiting thereof. The invention is defined by the following claims, with equivalents of the claims to be included therein.

What is claimed is:

1. A composition comprising an isolated *Lactobacillus paracasei* D3.5 strain or cellular components thereof, wherein said composition is provided in a nutritionally acceptable carrier,
wherein said carrier comprises a food product selected from yogurt, cheese, fermented milk, ice cream, chocolates, ready-to-eat desserts, and baked products.

2. The composition of claim 1, wherein said strain is lyophilized or freeze-dried.

3. The composition of claim 1, wherein said strain is non-viable.

4. The composition of claim 1, wherein said strain is present in the composition in an amount effective to treat leaky gut and/or inflammation.

5. The composition of claim 1, wherein said strain is present in the composition in an amount of from 1 million to 10 trillion.

6. The composition of claim 1, wherein said composition comprises cell wall components purified from the isolated *Lactobacillus paracasei* D3.5 strain.

7. A composition comprising lipoteichoic acid isolated from a *Lactobacillus paracasei* D3.5 strain, wherein said composition is provided in a nutritionally acceptable carrier,
wherein said carrier comprises a food product selected from yogurt, cheese, fermented milk, ice cream, chocolates, ready-to-eat desserts, and baked products.

8. The composition of claim 7, wherein said lipoteichoic acid is lyophilized or freeze-dried.

9. The composition of claim 7, wherein said lipoteichoic acid is present in the composition in an amount effective to increase gut mucin production and/or to treat leaky gut and/or inflammation.

10. A method of increasing gut mucin production in a subject in need thereof, comprising administering to the subject a therapeutically effective amount of a composition comprising an isolated *Lactobacillus paracasei* D3.5 strain or cellular components thereof, wherein the cellular components comprise lipoteichoic acid, and wherein said administering is by enteral administration.

11. The method of claim 10, wherein said administering is by oral administration.

12. A method of treating a gastrointestinal condition or inflammation in a subject in need thereof, comprising administering to the subject a therapeutically effective amount of a composition comprising an isolated *Lactobacillus paracasei* D3.5 strain or cellular components thereof, wherein the cellular components comprise lipoteichoic acid, and wherein said administering is by enteral administration.

13. The method of claim 12, wherein the treating is for an age-related gastrointestinal condition such as leaky gut, metabolic dysfunction and/or inflammation.

14. A method of making a food product comprising adding to ingredients of the food product a composition comprising an isolated *Lactobacillus paracasei* D3.5 strain or cellular components thereof.

15. The composition of claim 1, wherein said carrier comprises a food product selected from yogurt, cheese, fermented milk, and ice cream.

16. The composition of claim 1, wherein said carrier further comprises preservatives, stabilizers, dyes, and/or flavoring agents.

17. The composition of claim 7, wherein said carrier comprises a food product selected from yogurt, cheese, fermented milk, and ice cream.

18. The composition of claim 7, wherein said carrier further comprises preservatives, stabilizers, dyes, and/or flavoring agents.

* * * * *